United States Patent
Machida et al.

(10) Patent No.: US 8,759,007 B2
(45) Date of Patent: Jun. 24, 2014

(54) METHOD TO PRODUCE A RECEPTOR CHIP USING BIOTINYLATED PROTEIN

(75) Inventors: Sachiko Machida, Ibaraki (JP); Kiyoshi Hayashi, Ibaraki (JP); Ken Tokuyasu, Ibaraki (JP); Yoshikiyo Sakakibara, Ibaraki (JP); Shigeru Matsunaga, Ibaraki (JP)

(73) Assignee: National Food Research Institute, Ibaraki (JP)

( * ) Notice: Subject to any disclaimer, the term of this patent is extended or adjusted under 35 U.S.C. 154(b) by 0 days.

(21) Appl. No.: 12/636,434

(22) Filed: Dec. 11, 2009

(65) Prior Publication Data

US 2010/0167340 A1    Jul. 1, 2010

Related U.S. Application Data

(60) Division of application No. 10/765,466, filed on Jan. 26, 2004, now abandoned, which is a continuation-in-part of application No. 10/653,687, filed on Sep. 2, 2003, now abandoned.

(30) Foreign Application Priority Data

Sep. 2, 2002   (JP) ................... 2002-256691
Aug. 28, 2003  (JP) ................... 2003-304624

(51) Int. Cl.
*G01N 33/53*    (2006.01)
*C12P 21/00*    (2006.01)
*C40B 20/08*    (2006.01)
*C40B 40/10*    (2006.01)
*C40B 50/16*    (2006.01)

(52) U.S. Cl.
USPC ............ 435/7.1; 435/68.1; 506/6; 506/18; 506/31

(58) Field of Classification Search
None
See application file for complete search history.

(56) References Cited

U.S. PATENT DOCUMENTS

| | | | |
|---|---|---|---|
| 5,378,608 A | 1/1995 | Marui et al. .............. 435/7.5 |
| 5,395,587 A | 3/1995 | Brigham-Burke et al. .. 422/68.1 |
| 5,830,762 A | 11/1998 | Weindel .................... 436/8 |
| 5,932,433 A | 8/1999 | Schatz ...................... 435/15 |
| 5,932,445 A | 8/1999 | Lal et al. .................. 435/69.1 |
| 5,945,308 A | 8/1999 | Tang et al. ............... 435/69.1 |
| 5,969,123 A | 10/1999 | Holtzman ................. 536/23.1 |
| 6,500,938 B1 | 12/2002 | Au-Young et al. ........ 536/23.1 |
| 6,649,419 B1 | 11/2003 | Anderson ................. 436/526 |
| 6,756,228 B2 | 6/2004 | Tall et al. ................. 435/325 |
| 6,852,833 B1 * | 2/2005 | Machida et al. .......... 530/350 |
| 2002/0055139 A1 | 5/2002 | Holtzman et al. ........ 435/69.1 |
| 2003/0032076 A1 | 2/2003 | Duffy et al. .............. 435/7.92 |
| 2003/0143226 A1 | 7/2003 | Kobayashi et al. ....... 424/143.1 |
| 2004/0185059 A1 | 9/2004 | Yla-Herttuala et al. ... 424/185.1 |
| 2006/0294603 A1 | 12/2006 | Forsberg et al. .......... 800/14 |

FOREIGN PATENT DOCUMENTS

| | | |
|---|---|---|
| JP | 2001-261697 | 9/2001 |
| JP | 2002-17353 | 1/2002 |
| JP | 2003-169693 | 6/2003 |
| WO | WO 01/64862 | 9/2001 |

OTHER PUBLICATIONS

Misawa et al. Biopolymers (1999), vol. 51(4), pp. 297-307.*
Chen et al., "LOX-1, the receptor for oxidized low-density lipoprotein identified from endothelial cells: implications in endothelial dysfunction and atherosclerosis," *Pharmacology & Therapeutics* 95:89-100, 2002.
Kakutani et al., "Accumulation of LOX-1 Ligand in Plasma and Atherosclerotic Lesions of Watanabe Heritable Hyperlipidemic Rabbits: Identification by Novel Enzyme Immunoassay," *Biochemical and Biophysical Research Communications* 282:180-185, 2001.
Kataoka et al., "Biosynthesis and Post-translation Processing of Lectin-like Oxidized Low Density Lipoprotein Receptor-1 (LOX-1)," *The Journal of Biological Chemistry* 275(9):6573-6579, 2000.
Machida et al., "Reconstitition and characterization of ligand binding ability of Lectin-like Oxidized Low-density Lipoproteini Receptor-1," *National Food Research Institute* 74(9):281, 2002.
Moriwaki et al., "Ligand Specificity of LOX-1, a Novel Endothelial Receptor for Oxidized Low Density Lipoprotein," *Arterioscler Thromb Vasc Biol.* 18:1541-1547, 1998.
Muramatsu et al., "Piezoelectric Crystal Biosensor Modified with Protein A for Determination of Immunoglobulins," *Anal. Chem.* 59:2760-2763, 1987.
Murase et al., "Identification of Soluble Forms of Lectin-Like Oxidized LDL Receptor-1," *Arterioscler Thromb Vasc Biol*, 20:7215-720, 2000.
Oka et al., "Lectin-like oxidized low-density lipoprotein receptor 1 mediates phagocytosis of aged/apoptotic cells in endothelial cells," *Proc. Natl. Acad. Sci. USA* 95:9535-9540, 1998.
Weis et al., "The C-type lectin superfamily in the immune system," *Immunological Reviews* 163:19-34, 1998.
Machida et al., "A Method to Produce a Receptor Chip Using Biotinylated Protein," U.S. Appl. No. 10/765,466, Office action mailed Dec. 3, 2004.
Machida et al., "A Method to Produce a Receptor Chip Using Biotinylated Protein," U.S. Appl. No. 10/765,466, Office Action mailed Apr. 19, 2005.
Machida et al., "A Method to Produce a Receptor Chip Using Biotinylated Protein," U.S. Appl. No. 10/765,466, Office Action mailed Sep. 29, 2005.

(Continued)

*Primary Examiner* — Christine J Saoud
*Assistant Examiner* — Jegatheesan Seharaseyon
(74) *Attorney, Agent, or Firm* — Seed IP Law Group PLLC

(57) ABSTRACT

The present invention provides a method for detecting modified LDL, abnormal cells or bacteria using an intermolecular interaction analysis method, in which a region involved in ligand recognition by a receptor is expressed, without modification or as a biotinylated protein, in cells or in a test tube, and thereafter, the expressed region or the expressed biotinylated protein is immobilized via avidin or streptavidin to a solid phase while the orientation thereof is maintained, and the immobilized protein is utilized; and a kit for detecting the modified LDL or the like.

4 Claims, 5 Drawing Sheets

(56) References Cited

OTHER PUBLICATIONS

Machida et al., "A Method to Produce a Receptor Chip Using Biotinylated Protein," U.S. Appl. No. 10/765,466, Office Action mailed Jun. 12, 2006.

Machida et al., "A Method to Produce a Receptor Chip Using Biotinylated Protein," U.S. Appl. No. 10/765,466, Office Action mailed Feb. 7, 2007.

Machida et al., "A Method to Produce a Receptor Chip Using Biotinylated Protein," U.S. Appl. No. 10/765,466, Office Action mailed Aug. 2, 2007.

Machida et al., "A Method to Produce a Receptor Chip Using Biotinylated Protein," U.S. Appl. No. 10/765,466, Office Action mailed Jan. 25, 2008.

Machida et al., "A Method to Produce a Receptor Chip Using Biotinylated Protein," U.S. Appl. No. 10/765,466, Office Action mailed Jul. 18, 2008.

Machida et al., "A Method to Produce a Receptor Chip Using Biotinylated Protein," U.S. Appl. No. 10/765,466, Office Action mailed Jan. 8, 2009.

Machida et al., "A Method to Produce a Receptor Chip Using Biotinylated Protein," U.S. Appl. No. 10/765,455, Office Action mailed Sep. 11, 2009.

Schendel, "Overview of protein expression in *E. coli*," *Curr Protoc Mol Biol* Chapter 16:Unit 16.1, 2002, (abstract).

Swartz, "Advances in *Escherichia coli* production of therapeutic proteins," *Curr Opin Biotechnol* 12(2):195-2001, 2001, (abstract).

\* cited by examiner

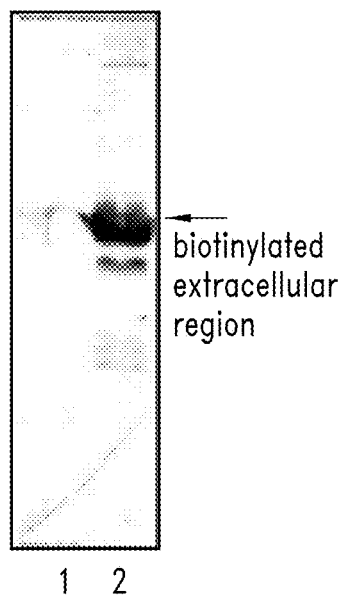
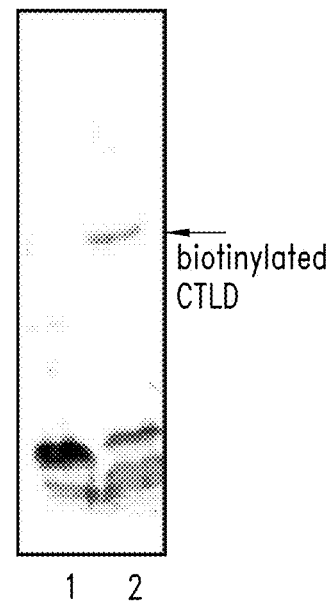
*FIG. 1A*  *FIG. 1B*

US 8,759,007 B2

METHOD TO PRODUCE A RECEPTOR CHIP USING BIOTINYLATED PROTEIN

CROSS-REFERENCE TO RELATED APPLICATIONS

This application is a divisional of U.S. patent application Ser. No. 10/765,466, filed Jan. 26, 2004 now abandoned; which is a continuation-in-part of U.S. patent application Ser. No. 10/653,687, filed Sep. 2, 2003, now abandoned; which claims priority to Japanese Application No. 2002-256691 filed Sep. 2, 2002; and Japanese Application No. 2003-304624 filed Aug. 28, 2003; all of which applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690115_401D1a_SEQUENCE_LISTING.txt. The text file is 12 KB, was created on Mar. 8, 2010, and is being submitted electronically via EFS-Web.

BACKGROUND OF THE INVENTION

1. Field of the Invention

The present invention relates to a method for producing a receptor chip by immobilizing a biotinylated recombinant receptor protein on a chip, a detection kit comprising the receptor chip, and a receptor chip produced by the method.

The present invention relates to a receptor chip produced by expressing a region of a scavenger receptor relating to a ligand recognition site which is used as a receptor fragment, in vivo or in vitro, and immobilizing the fragment on a solid phase. The receptor chip is useful as a high-sensitivity receptor chip for detection of modified LDL (Low Density Lipoprotein), such as oxidized LDL, acetylated LDL, succinylated LDL, and malondialdehyde LDL, glycosylated LDL, or the like, abnormal cells, and bacteria.

The present invention relates to a method and kit for detecting modified LDL, abnormal cells (e.g., apoptotic cells, etc.), or bacteria. To obtain this invention, an extracellular region and a C-type lectin-like domain (CTLD) of a scavenger receptor is expressed in cells (e.g., $E.\ coli$ or the like) or in test tubes as biotinylated proteins. Thereafter, the erroneous structure of an inactive aggregate of biotinylated protein is unfolded with a denaturant. The protein is refolded with a detergent and a cyclic carbohydrate into a correct higher-order structure. The resultant protein is immobilized via avidin, streptavidin, or the like, on solid phase while keeping an appropriate direction thereof. The thus-obtained solid phase is employed as a sensor portion (detection sensor) in an intermolecular interaction analysis method, for example, a detection method using a detector, such as, a surface plasmon resonance device, a quartz-crystal microbalance device, or the like.

According to the present invention, it is possible to produce a receptor chip on which any receptor or a receptor fragment is immobilized.

2. Description of the Related Art

Receptors present on a cell surface specifically bind with ligands corresponding to the receptors. As a result, various signals are transduced into cells. There are a variety of receptors present on a cell surface and the corresponding receptors are different from one another. Therefore, in order to detect and/or quantitate a specific ligand, it is useful to use a receptor capable of being specifically binding with the ligand. If a receptor chip is produced whose ligand is a diagnostic marker for abnormal cells or diseases, it is expected to provide a tool useful for the detection of abnormal cells in a cell population or for the diagnosis of diseases.

For example, a plurality of receptors capable of recognizing and binding modified LDL accumulated in an organism, and abnormal cells such as apoptotic cells or aged erythrocytes, bacteria invading an organism, or the like have been found. Among these receptors, there are a number of receptors whose region required for recognition of a ligand has been conjectured. There is a possibility that by employing these receptors themselves or only regions thereof required for recognition, ligands, i.e., modified LDL, abnormal cells (e.g., apoptotic cells, etc.), and bacteria can be easily detected.

There is a demand for the production of a high-sensitivity ligand sensor in which a region of a receptor relating to the ligand recognition site is immobilized on a solid phase, such as a chip, for ligand recognition utilizing a receptor.

However, receptor proteins are generally expressed in a small amount. Therefore, it is difficult to prepare a large amount of a native receptor protein to such an extent that a receptor chip can be produced. Further, when a recombinant expression system is employed, since a receptor is a membrane protein, a region essentially required for recognition needs to be obtained as a soluble protein in order to construct a system capable of detection. In addition, the thus-obtained soluble protein needs to be modified so that it can serve as a sensor capable of detection.

However, in conventional techniques, it is difficult to obtain a soluble protein itself. A most simple, efficient, and inexpensive method for obtaining a soluble protein is to express a protein of interest using genetic engineering techniques, particularly using $E.\ coli$ as a host. However, with this method, expression products are accumulated in bacteria as an inactive aggregate called an inclusion body, and therefore, it is not possible to obtain a soluble protein.

Animal cells may be employed as hosts to obtain a soluble protein useful for measurement of a ligand. For example, Japanese Laid-Open Publication No. 2002-17353 discloses a method for quantitating modified LDL using a receptor. Specifically, an animal cell is used to express a fusion protein comprising an extracellular region of an oxidized LDL receptor and a part of the constant region of an immunoglobulin heavy chain. By detecting the fusion protein with an immunoassay, an oxidized LDL can be quantitated with high sensitivity. However, such a method using animal culture cells requires much labor and cost.

An attempt has been made to refold an aggregate derived from a receptor protein accumulated in $E.\ coli$ into a soluble correct structure (e.g., Japanese Laid-Open Publication No. 2003-169693 relating to soluble IL-15 receptor α chain). However, in conventional methods, for example, after a receptor is adsorbed onto a resin, the resultant resin is contacted with a buffer solution containing a denaturant and then with buffer solutions having a gradually reduced concentration of a denaturant (Japanese Laid-Open Publication No. 2003-169693). Thus, conventional methods are complicated. Further, when a protein is refolded as it is immobilized on a solid phase, the step of eluting or cleaving the protein from the solid phase, or the like, is required after refolding, resulting in an increase in method complexty, a reduction in yield, and the like. Furthermore, the obtained soluble protein was not appropriately modified for use in a detection system no matter whether a solid phase was used. It was not possible to immobilize a refolded protein at a desired position.

It is known that addition of a His tag or a GST tag, or biotinylation of an expression product are used for immobilization of proteins based on affinity. Among these techniques, protein biotinylation is preferable because of less steric hindrance and less influence from metal ions and reducing agents. Biotinylation needs to be carried out within bacteria in order to achieve efficient biotinylation without impairing the function of expression products. However, conventional techniques have difficulty in refolding products expressed under conditions which permit generation of inclusion bodies, and a low expression level and degradation of products expressed under conditions that do not permit generation of inclusion bodies. Therefore, a receptor chip has not been produced by expression and immobilization of biotinylated receptor proteins.

For the above-described reasons, a method has not been currently established to produce a receptor, which can be easily immobilized on a solid phase while keeping the ability of being bound to a ligand.

SUMMARY OF THE INVENTION

The present inventor found that: a recombinantly expressed biotinylated receptor protein was refolded in a solution containing a cyclic carbohydrate (cycloamylose) and a polyoxyethylene detergent or a solution containing a cyclic carbohydrate (cycloamylose) and an ionic detergent, and the refolded protein was immobilized on a solid phase, whereby a recombinantly expressed biotinylated receptor protein could be easily immobilized on a solid phase while keeping the ability of being bound to a ligand.

Further, we found that an extracellular region and CTLD of hLOX (a receptor for a C-type lectin-like oxidized LDL of the scavenger receptor family) were accumulated in large amounts within *E. coli*; and thereafter, these components were reconstituted into a soluble protein, which was in turn utilized as a sensor portion for detection of modified LDL, abnormal cells such as apoptotic cells, bacteria, and the like. Thus, we reached the present invention.

Thus, the present invention provides the following.

1. A receptor chip, on which a recombinantly expressed biotinylated receptor protein is immobilized via a factor capable of specifically binding to biotin.
2. A receptor chip according to item 1, wherein the biotinylated receptor protein is expressed in a bacterial host.
3. A receptor chip according to item 1, wherein the biotinylated receptor protein is expressed in vitro.
4. A receptor chip according to item 2, wherein the biotinylation of the receptor protein is carried out within a bacterial host.
5. A receptor chip according to item 2, wherein the biotinylation of the receptor protein is carried out in vitro after expression of the protein.
6. A receptor chip according to item 4, wherein the immobilized biotinylated receptor protein is obtained by refolding a biotinylated receptor protein expressed as an inclusion body within a bacterium.
7. A receptor chip according to item 6, wherein the refolding is carried out in a solution containing a cyclic carbohydrate cycloamylose and a polyoxyethylene detergent.
8. A receptor chip according to item 7, wherein the degree of polymerization of the cyclic carbohydrate cycloamylose is 17 to 50 or 40 to 150.
9. A receptor chip according to item 8, wherein the degree of polymerization of the cyclic carbohydrate cycloamylose is 40 to 150.
10. A receptor chip according to item 7, wherein the polyoxyethylene detergent is polyoxyethylenesorbitan ester, polyoxyethylenedodecyl ether, polyoxyethylenehepta methylhexyl ether, polyoxyethyleneisooctylphenyl ether, polyoxyethylenenonylphenyl ether, polyoxyethylene fatty acid ester, or sucrose fatty acid ester.
11. A receptor chip according to item 6, wherein the refolding is carried out in a solution containing a cyclic carbohydrate cycloamylose and an ionic detergent.
12. A receptor chip according to item 11, wherein the degree of polymerization of a cyclic carbohydrate cycloamylose is 17 to 50 or 40 to 150.
13. A receptor chip according to item 12, wherein the degree of polymerization of a cyclic carbohydrate cycloamylose is 40 to 150.
14. A receptor chip according to item 11, wherein the ionic detergent is cetyltrimethyl ammonium bromide, dodecyl sodium sulfate, sodium deoxycholate, 3-[(3-cholamidopropyl)dimethylammonio]-1-propane sulfonate, hexadecyltrimethyl ammonium bromide, or myristyl sulfo betaine.
15. A receptor chip according to item 1, wherein the receptor is selected from the group consisting of scavenger receptors, receptors of the insulin receptor family, receptors of the EGF receptor family, receptors of the PDGF receptor family, receptors of the VEGF receptor family, receptors of the FGF receptor family, growth factor receptors of the NGF receptor family, TGF-β super family receptors, Toll-like receptor family, LDL receptors related protein family, and receptors of the G protein coupled receptor family.
16. A receptor chip according to item 15, wherein the receptor is a scavenger receptor LOX-1.
17. A receptor chip according to item 1, adapted for detection using surface plasmon resonance, quartz-crystal microbalance, or mass spectrometer.
18. A method for producing a receptor chip, comprising the steps of:
 a) recombinantly expressing a biotinylated receptor protein as an inclusion body within a bacterial host;
 b) refolding the inclusion body in a solution containing a cyclic carbohydrate cycloamylose and a polyoxyethylene detergent to prepare a soluble biotinylated receptor protein; and
 c) immobilizing the refolded soluble biotinylated receptor protein to a solid phase via a factor capable of specifically binding to biotin.
19. A method according to item 18, wherein the degree of polymerization of the cyclic carbohydrate cycloamylose is 17 to 50 or 40 to 150.
20. A method according to item 19, wherein the degree of polymerization of the cyclic carbohydrate cycloamylose is 40 to 150.
21. A method according to item 18, wherein the polyoxyethylene detergent is polyoxyethylenesorbitan ester, polyoxyethylenedodecyl ether, polyoxyethyleneheptamethylhexyl ether, polyoxyethyleneisooctylphenyl ether, polyoxyethylenenonylphenyl ether, polyoxyethylene fatty acid ester, or sucrose fatty acid ester.
22. A method according to item 18, wherein the receptor is selected from the group consisting of scavenger receptors, receptors of the insulin receptor family, receptors of the EGF receptor family, receptors of the PDGF receptor family, receptors of the VEGF receptor family, receptors of the FGF receptor family, growth factor receptors of the NGF receptor family, TGF-β super family receptors, Toll-like receptor family, LDL receptors related protein family, and receptors of the G protein coupled receptor family.

23. A method according to item 22, wherein the receptor is a scavenger receptor LOX-1.

24. A method according to item 18, wherein the solid phase is adapted for detection using surface plasmon resonance, quartz-crystal microbalance, or mass spectrometer.

25. A method for producing a receptor chip, comprising the steps of:
   a) recombinantly expressing a biotinylated receptor protein as an inclusion body within a bacterial host;
   b) refolding the inclusion body in a solution containing a cyclic carbohydrate cycloamylose and an ionic detergent to prepare a soluble biotinylated receptor protein; and
   c) immobilizing the refolded soluble biotinylated receptor protein to a solid phase via a factor capable of specifically binding to biotin.

26. A method according to item 25, wherein the degree of polymerization of the cyclic carbohydrate cycloamylose is 17 to 50 or 40 to 150.

27. A method according to item 26, wherein the degree of polymerization of the cyclic carbohydrate cycloamylose is 40 to 150.

28. A method according to item 25, wherein the ionic detergent is cetyltrimethyl ammonium bromide, dodecyl sodium sulfate, sodium deoxycholate, 3-[(3-cholamidopropyl)dimethylammonio]-1-propane sulfonate, hexadecyltrimethyl ammonium bromide, or myristyl sulfo betaine.

29. A method according to item 25, wherein the receptor is selected from the group consisting of scavenger receptors, receptors of the insulin receptor family, receptors of the EGF receptor family, receptors of the PDGF receptor family, receptors of the VEGF receptor family, receptors of the FGF receptor family, growth factor receptors of the NGF receptor family, TGF-β super family receptors, Toll-like receptor family, LDL receptors related protein family, and receptors of the G protein coupled receptor family.

30. A method according to item 29, wherein the receptor is a scavenger receptor LOX-1.

31. A method according to item 25, wherein the solid phase is adapted for detection using surface plasmon resonance, quartz-crystal microbalance, or mass spectrometer.

32. A receptor chip produced by a method according to item 18 or 25.

33. A method for detecting modified LDL, an abnormal cell, or a bacterium, using a receptor chip according to item 16.

34. A receptor chip produced by a method according to item 23 or 30.

35. A method for detecting modified LDL, an abnormal cell, or a bacterium, using a receptor chip according to item 34.

36. A detection kit, comprising a receptor chip produced by a method according to item 18 or 25.

37. A detection kit, comprising a receptor chip according to item 16.

38. A detection kit, comprising a receptor chip produced by a method according to item 23 or 30.

39. A detection kit, comprising a receptor chip according to item 34.

The present invention also provides a method for detecting modified LDL, abnormal cells, or bacteria by an intermolecular interaction analysis method using a recombinant protein obtained by expressing a region of a receptor relating to ligand recognition in vivo or in vitro.

The present invention also provides a method for detecting modified LDL, abnormal cells, or bacteria by an intermolecular interaction analysis method using an immobilized protein obtained by expressing a region of a receptor relating to ligand recognition as a biotinylated protein in vivo or in vitro, and immobilizing the expressed biotinylated protein on a solid phase via avidin or streptavidin while keeping an appropriate orientation of the protein.

The present invention also provides a method for detecting modified LDL, abnormal cells, or bacteria by an intermolecular interaction analysis method using a reconstituted protein obtained by refolding an extracellular region or ligand recognition region of a receptor accumulated in E. coli into a correct three-dimensional structure.

The present invention also provides a method for detecting modified LDL, abnormal cells, or bacteria by an intermolecular interaction analysis method using a immobilized protein obtained by refolding a biotinylated extracellular region or biotinylated ligand recognition region of a receptor accumulated in E. coli into a correct three-dimensional structure, and immobilizing the reconstituted biotinylated protein on a solid phase via avidin or streptavidin while keeping an appropriate direction of the protein.

The present invention also provides a kit for detecting modified LDL, abnormal cells, or bacteria, comprising a protein obtained by unfolding the structure of an extracellular region or ligand recognition region of receptor accumulated as an aggregate in E. coli with a denaturant, and refolding the protein into a correct three-dimensional structure with a detergent and a cyclic carbohydrate.

The present invention also provides a kit for detecting modified LDL, abnormal cells, or bacteria, comprising a solid phase with a protein, where the protein is obtained by unfolding the structure of an biotinylated extracellular region or biotinylated ligand recognition region of receptor accumulated as an aggregate in E. coli with a denaturant, and refolding the protein into a correct three-dimensional structure with a detergent and a cyclic carbohydrate, and the protein is immobilized on the solid phase via avidin or streptavidin while keeping an appropriate orientation of the protein.

Thus, the invention described herein makes possible the advantages of providing a receptor chip produced by preparing a large amount of biotinylated receptor proteins capable of being easily immobilized on a solid phase and immobilizing the proteins on a solid phase; a detection kit and detection method using the chip; a method for detecting modified LDL, abnormal cells, and bacteria using a receptor chip comprising a scavenger receptor; and a method and kit for detecting modified LDL, abnormal cells (e.g., apoptotic cells, aged erythrocytes, etc.), bacteria invading an organism, and the like, using a sensor portion utilizing the ligand recognition characteristic of the protein by preparing a large amount of soluble ligand recognition regions, which can be immobilized on a solid phase, preferably keeping an appropriate direction of the protein (a ligand binding site is directed toward the outside).

These and other advantages of the present invention will become apparent to those skilled in the art upon reading and understanding the following detailed description with reference to the accompanying figures.

BRIEF DESCRIPTION OF THE DRAWINGS

FIG. 1 shows an image of electrophoresis indicating the expression of a biotinylated extracellular region and a biotinylated CTLD in Example 1. A: Biotinylated extracellular region. B: Biotinylated CTLD. Lane 1: Insoluble fraction. Lane 2: Soluble fraction.

DESCRIPTION OF THE PREFERRED EMBODIMENTS

Figure 2A:
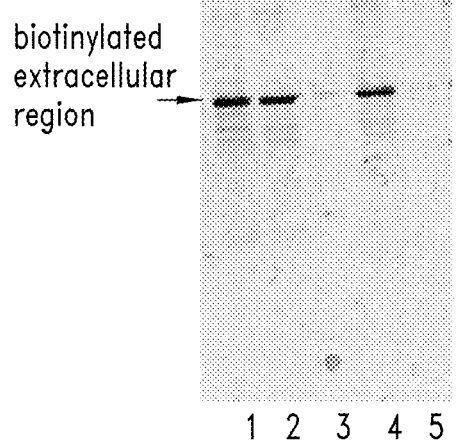
FIG. 2 shows an image of an electrophoresis gel indicating the result of refolding of a biotinylated extracellular region and a biotinylated CTLD in Example 2. A: Biotinylated extracellular region. B: Biotinylated CTLD. Lane 1: Inclusion body. Lane 2: Protein recovered in a soluble fraction using CTAB. Lane 3: Protein recovered in an insoluble fraction using CTAB. Lane 4: Protein recovered in a soluble fraction using SB3-14. Lane 5: Protein recovered in an insoluble fraction using SB3-14.

Hereinafter, the present invention will be described. It must be noted that, as used in this specification and the appended claims, the singular forms "a", "an" and "the" include plural referents unless the content clearly dictates otherwise. It should be also understood that terms as used herein have definitions ordinarily used in the art unless otherwise mentioned. Contents of all cited documents are incorporated herein as reference.

Hereinafter, definitions of the terms as used herein particularly will be listed.

The term "receptor" as used herein refers to a biological structure comprising one or more binding domains which can complex with one or more ligands reversibly and specifically, and the complexation has a biological structure. The receptor may be entirely outside a cell (an extracellular receptor), entirely inside a cell membrane (a portion of receptor is directed to an environment outside the cell and to the cytosol), or entirely inside a cell (intracellular receptor). The receptor may function independently of the cell. The receptor inside the cell membrane provides communication between the inside of the cell membrane and a space outside the cell membrane (for example, signal transduction), and allows the cell to function in transportation of molecules and ions to inside and outside the cell. As used herein, the receptor may be a receptor of full length, or may be a receptor fragment.

When the receptor fragment is used, a site related to ligand recognition of a receptor protein can be used. The site related to ligand recognition of a receptor protein may be identified as follows. The ligand recognition region can be estimated from the structure of a protein highly similar in homology and in function by homology or domain search. For example, when amino acid sequences of different receptor molecules which specifically bind to the same ligand is calculated using a default parameter of BLAST, a region indicating homology of 50% or higher, preferably 55% or higher, more preferably 60% or higher, still more preferably 65% or higher, is estimated as a ligand recognition region. Further, those skilled in the art can readily perform transient expression of a gene encoding a mutant receptor to which a deficient mutation or amino acid substitution is introduced in an animal cell or the like, to determine a region essential for the function thereof.

The term "ligand" as used herein is a binding partner to a specific receptor or a family of a receptors. The ligand may be an endogenous ligand, or alternately, a synthesized ligand to a receptor such as a drug, a candidate for a drug, or pharmacological means.

The terms "protein", "polypeptide", "oligopeptide", and "peptide" as used herein have the same meaning and refer to a polymer of amino acids having any length. The polymer may be a straight chain, branched, or cyclic. The amino acid may be a naturally-occurring, non-naturally-occurring, or modified amino acid. Those referred by these terms may also assemble to a plurality of polypeptide chain complexes. Those referred by these terms also include a naturally or artificially modified amino acid polymer. Such a modification includes, for example, disulfide bond formation, glycosylation, lipidation, acetylation, phosphorylation and any other operation or modification (for example, conjugation with a labeling component). This definition also includes, for example, a polypeptide including one or more analogs of amino acid (for example, including non-naturally-occurring amino acid or the like), a peptide-like compound (for example, peptoid), and other modifications known in the art.

The terms "polynucleotide", "oligonucleotide", and "nucleic acid" as used herein have the same meaning and refer to a nucleotide polymer having any length. This term also includes an "oligonucleotide derivative" or a "polynucleotide derivative". An "oligonucleotide derivative" or a "polynucleotide derivative" includes a nucleotide derivative, or refers to an oligonucleotide or a polynucleotide having different linkages between nucleotides from typical linkages, which are interchangeably used. Examples of such an oligonucleotide specifically include 2'-O-methyl-ribonucleotide, an oligonucleotide derivative in which a phosphodiester bond in an oligonucleotide is converted to a phosphorothioate bond, an oligonucleotide derivative in which a phosphodiester bond in an oligonucleotide is converted to an N3'-P5' phosphoroamidate bond, an oligonucleotide derivative in which a ribose and a phosphodiester bond in an oligonucleotide are converted to a peptide-nucleic acid bond, an oligonucleotide derivative in which uracil in an oligonucleotide is substituted with C-5 propynyl uracil, an oligonucleotide derivative in which uracil in an oligonucleotide is substituted with C-5 thiazole uracil, an oligonucleotide derivative in which cytosine in an oligonucleotide is substituted with C-5 propynyl cytosine, an oligonucleotide derivative in which cytosine in an oligonucleotide is substituted with phenoxazine-modified cytosine, an oligonucleotide derivative in which ribose in DNA is substituted with 2'-O-propyl ribose, and an oligonucleotide derivative in which ribose in an oligonucleotide is substituted with 2'-methoxyethoxy ribose. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be produced by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

As used herein, "nucleic acid" is also used interchangeably with gene, cDNA, mRNA, oligonucleotide and polynucleotide. A particular nucleic acid sequence also includes "splice variant". Similarly, a particular protein encoded by a nucleic acid implicitly encompasses any protein encoded by a splice variant of that nucleic acid. "Splice variants", as the name suggests, are products of alternative splicing of a gene. After transcription, an initial nucleic acid transcript may be spliced such that different (alternative) nucleic acid splice products encode different polypeptides. Mechanisms for the production of splice variants vary, but include alternative splicing of exons. Different polypeptides derived from the same nucleic acid by read-through transcription are also encompassed by this definition. Any products of a splicing reaction, including recombinant forms of the splice products, are included in this definition.

As used herein, "gene" refers to an agent defining a genetic trait. A gene is typically arranged in a given sequence on a chromosome. A gene which defines a primary structure of a protein is called a structural gene. A gene which regulates the expression of a structural gene is called a regulatory gene. As used herein, "gene" may refer to "polynucleotide", "oligonucleotide", and "nucleic acid" and/or "protein", "polypeptide", "oligopeptide" and "peptide". As used herein, "homology" of genes with respect to a gene refers to the degree of identity between two or more gene sequences. Therefore, the greater the homology between two given genes, the greater the identity or similarity between their sequences. Whether or not two genes have homology is determined by comparing their sequences directly or, in the case of nucleic acids, by a hybridization method under stringent conditions. When two gene sequences are directly compared with each other, these genes have homology if the DNA sequences of the genes have typically at least 50% identity, preferably at least 70% identity, more preferably at least 80%, 90%, 95%, 96%, 97%, 98%, or 99% identity with each other.

The identity and homology of base sequences are herein calculated using a sequence analyzing tool, BLAST, with the default parameters.

As used herein, the term "expression" of a gene, a polynucleotide, a polypeptide, or the like, indicates that the gene or the like undergo certain processes in vivo to be changed into another form. Preferably, the term "expression" indicates that genes, polynucleotides, or the like are transcribed and translated into polypeptides. In one embodiment of the present invention, the term "expression" refers to the event wherein genes are transcribed to produce mRNA. More preferably, these polypeptides may have post-translational processing modifications.

As used herein, "amino acid" may refer to a naturally-occurring or nonnaturally-occurring amino acid. The term "amino acid derivative" or "amino acid analog" refers to an amino acid which is different from a naturally-occurring amino acid and has a function similar to that of the original amino acid. Such an amino acid derivative and amino acid analog are well known in the art. The term "naturally-occurring amino acid" refers to an L-isomer of a naturally-occurring amino acid. The naturally-occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine, and lysine. Unless otherwise indicated, all amino acids as used herein are L-isomers. The term "nonnaturally-occurring amino acid" refers to an amino acid which is not ordinarily found in proteins in the nature. Examples of nonnaturally-occurring amino acids include norleucine, para-nitrophenylalanine, homophenylalanine, para-fluorophenylalanine, 3-amino-2-benzil propionic acid, D- or L-homoarginine, and D-phenylalanine. The term "amino acid analog" refers to a molecule having a physical property and/or function similar to that of amino acids, but not an amino acid. Examples of amino acid analogs include, for example, ethionine, canavanine, 2-methylglutamine, and the like. An amino acid mimic refers to a compound which has a structure different from that of the general chemical structure of amino acids but which functions in a manner similar to that of naturally-occurring amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "corresponding" amino acid refers to an amino acid in a given protein molecule or polypeptide molecule, which has, or is anticipated to have, a function similar to that of a predetermined amino acid in a protein or polypeptide as a reference for comparison. Particularly, in the case of enzyme molecules, the term refers to an amino acid which is present at a similar position in an active site and similarly contributes to catalytic activity.

As used herein, the term "nucleotide" may be either naturally-occurring or nonnaturally-occurring. The term "nucleotide derivative" or "nucleotide analog" refers to a nucleotide which is different from a naturally-occurring nucleotide and has a function similar to that of the original nucleotide. Such a nucleotide derivative and nucleotide analog are well known in the art. Examples of such a nucleotide derivative and nucleotide analog include, but are not limited to, phosphorothioate, phosphoramidate, methylphosphonate, chiral-methylphosphonate, 2-O-methyl ribonucleotide, and peptide-nucleic acid (PNA).

As used herein, the term "fragment" refers to a polypeptide or polynucleotide having a sequence length ranging from 1 to n−1 with respect to the full length of the reference polypeptide or polynucleotide (of length n). The length of the fragment can be appropriately changed depending on the purpose. For example, in the case of polypeptides, the lower limit of the length of the fragment includes 3, 4, 5, 6, 7, 8, 9, 10, 15, 20, 25, 30, 40, 50 or more amino acids. Lengths represented by integers which are not herein specified (e.g., 11 and the like) may be appropriate as a lower limit. In the case of polynucleotides, the lower limit of the length of the fragment includes 5, 6, 7, 8, 9, 10, 15, 20, 25, 30, 40, 50, 75, 100 or more nucleotides. Lengths represented by integers which are not herein specified (e.g., 11 and the like) may be appropriate as a lower limit. As used herein, preferably, receptor "fragment" specifically binds to a ligand to which a full-length receptor can specifically bind. A preferable fragment of a C-type lectin-like oxidized LDL is a fragment including C-type lectin-like domain (CTLD).

One of the methods for producing the polypeptide of the present invention is, for example, a method in which bacteria (prokaryotes) producing the polypeptide are cultured, a recombinant receptor protein is accumulated in the bacteria as an inclusion body, and then the host bacteria are disrupted so as to obtain the polypeptide.

One of amino acid sequences of biotinylation motifs for biotinylating a protein in *E. coli* is: "MKLKVTVNGTAYD-VDVDVDKSHENPMGTILFGGGTGGAPA-PAAGGAGAGKAGEG EIPAPLAGTVSKILVKEGDTVK- AGQTVLVLEAMKMETEINAPTDGKVEKVLVKER DAVQGGQGLIKIGDLEL" (SEQ ID NO:5). An amino acid sequence "GLNDIFEAQKIEWHE" (SEQ ID NO:6) also can be used as a biotinylation motif. In these sequences, when mutation is introduced to portions other than K(lysine) residue, the residue which is actually biotinylated, biotinylation activity is not largely affected. Thus, sequences having portions other than lysine residue substituted can also be used as a biotinylation motif. Furthermore, biotinylation by adding "KIG, KI, KIA, KIE, KIGDP (SEQ ID NO:7), KLWSI (SEQ ID NO:8), KLG, KVG" or the like including K which is actually biotinylated to the C-terminal is also possible.

It is also possible to purify an exogenous protein to be expressed by introducing a recognition sequence "IEGR" (SEQ ID NO:9) of Factor Xa which is an endoproteinase, recognition sequence "DDDDK" (SEQ ID NO:10) of an enterokinase or the like between such biotinylation motifs and the exogenous protein and then cleave with the Factor Xa or the enterokinase. For example, for expressing CTLD, the amino acid sequence "IEGR" may be introduced between such biotinylation motifs and CTLD to purify only CTLD.

As used herein, the term "transformant" refers to the whole or a part of an organism, such as a cell, which is produced by transforming a host cell. An Example of a transformant includes a prokaryotic cell. Transformants may be referred to as transformed cells, transformed tissue, transformed hosts, or the like, depending on the subject. As used herein, transformants include all of these forms, but in a particular context, it refers to a particular form.

A host bacteria cell for obtaining a transformant is not particularly limited as long as it can express a polypeptide maintaining a physiological activity. Any type of host bacteria cells which has been conventionally used in genetic engineering can be used. Examples of the prokaryotic cells include prokaryotic cells which belong to *Escherichia, Serratia, Bacillus, Brevibacterium, Corynebacterium, Microbacterium, Pseudomonas*, or the like, for example, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* BL21 (DE3), *Escherichia coli* BL21 (DE3)pLysS, *Escherichia coli* HMS174 (DE3), *Escherichia coli* HMS174 (DE3)pLysS, *Serratia ficaria, Serratia fonticola, Serratia liquefaciens, Serratia marcescens, Bacillus subtilis, Bacillus amyloliquefaciens, Brevibacterium ammmoniagenes, Brevibacterium immariophilum* ATCC14068, *Brevibacterium saccharolyticum* ATCC14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, *Pseudomonas* sp. D-0110, and the like.

The polypeptide derived from the cells obtained in the present invention, as long as it has an activity substantially the same as the activity of a naturally-occurring type polypeptide, may have one or more amino acids in the amino acid sequence substituted, added, and/or deleted, and a carbohydrate chain may be substituted, added, and/or deleted.

A given amino acid contained in a sequence may be substituted with another amino acid in a protein structure, such as a ligand molecule binding site, without a clear reduction or loss of interactive binding ability. A given biological function of a protein is defined by the interactive ability or other property of the protein. Therefore, a particular amino acid substitution may be performed in an amino acid sequence, or at the DNA code sequence level, to produce a protein which maintains the original property after the substitution. Therefore, various modifications of peptides as disclosed herein and corresponding DNA encoding such peptides may be performed without clear losses of biological usefulness.

When the above-described modifications are designed, the hydrophobicity indices of amino acids may be taken into consideration. The hydrophobic amino acid indices play an important role in providing a protein with an interactive biological function, which is generally recognized in the art (Kyte. J and Doolittle, R. F., J. Mol. Biol. 157(1):105-132, 1982). The hydrophobic property of an amino acid contributes to the secondary structure of a protein produced and then regulates interactions between the protein and other molecules (e.g., enzymes, substrates, receptors, DNA, antibodies, antigens, etc.). Each amino acid is given a hydrophobicity index based on the hydrophobicity and charge properties thereof as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well known that if a given amino acid is substituted with another amino acid having a similar hydrophobicity index, a resultant protein may still have a biological function similar to that of the original protein (e.g., a protein having an equivalent ligand-binding activity). For such an amino acid substitution, the hydrophobicity index is preferably within ±2, more preferably within ±1, and even more preferably within ±0.5. It is understood in the art that such an amino acid substitution based on the hydrophobicity is efficient. As described in U.S. Pat. No. 4,554,101, amino acid residues are given the following hydrophilicity indices: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid may be substituted with another amino acid which has a similar hydrophilicity index and can still provide a biological equivalent. For such an amino acid substitution, the hydrophilicity index is preferably within ±2, more preferably ±1, and even more preferably ±0.5.

The term "conservative substitution" as used herein refers to amino acid substitution in which a substituted amino acid and a substituting amino acid have similar hydrophilicity indices or/and hydrophobicity indices. Examples of conservative substitutions include, but are not limited to, substitutions within each of the following residue groups: arginine and lysine; glutamic acid and aspartic acid; serine and threonine; glutamine and asparagine; and valine, leucine, and isoleucine, which are well known to those skilled in the art.

As used herein, the term "variant" refers to a substance, such as a polypeptide, polynucleotide, or the like, which differs partially from the original substance. Examples of such a variant include a substitution variant, an addition variant, a deletion variant, a truncated variant, an allelic variant, and the like. The term "allele" as used herein refers to a genetic variant located at a locus identical to a corresponding gene, where the two genes are distinguished from each other. Therefore, the term "allelic variant" as used herein refers to a variant which has an allelic relationship with a given gene. The term "species homolog" or "homolog" as used herein refers to one that has an amino acid or nucleotide homology with a given gene in a given species (preferably at least 60% homology, more preferably at least 80%, at least 85%, at least 90%, and at least 95% homology). A method for obtaining such a species homolog is clearly understood from the description of the present specification. The term "orthologs" (also called orthologous genes) refers to genes in different species derived from a common ancestry (due to speciation). For example, in the case of the hemoglobin gene family having multigene structure, human and mouse α-hemoglobin genes are orthologs, while the human α-hemoglobin gene and the human β-hemoglobin gene are paralogs (genes arising from gene duplication). Orthologs are useful for estimation of molecular phylogenetic trees. Therefore, orthologs may be useful in the present invention.

As used herein, the term "conservative (or conservatively modified) variant" applies to both amino acid and nucleic acid sequences. With respect to particular nucleic acid sequences, conservatively modified variants refer to those nucleic acids which encode identical or essentially identical amino acid sequences, and in the case where the nucleic acids do not encode amino acid sequences, refer to the essentially identical sequences. Because of the degeneracy of the genetic code, a large number of functionally identical nucleic acids encode any given protein. For example, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" which represent one species of conservatively modified variation. Every nucleic acid sequence herein which encodes a polypeptide also describes every possible silent variation of the nucleic acid. Those skilled in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence. Preferably, such modification may be performed while avoiding substitution of cysteine which is an amino acid capable of largely affecting the higher-order structure of a polypeptide.

Such a nucleic acid may be obtained by a well-known PCR method, or may be synthesized chemically. These methods may be combined with, for example, site-directed mutagenesis, hybridization method or the like.

In the present specification, in order to prepare functionally equivalent polypeptides, amino acid additions, deletions, or modifications can be performed in addition to amino acid substitutions. Amino acid substitution(s) refers to the replacement of at least one amino acid of an original peptide with different amino acids, such as the replacement of 1 to 10 amino acids, preferably 1 to 5 amino acids, and more preferably 1 to 3 amino acids with different amino acids. Amino acid addition(s) refers to the addition of at least one amino acid to an original peptide chain, such as the addition of 1 to 10 amino acids, preferably 1 to 5 amino acids, and more preferably 1 to 3 amino acids to an original peptide chain. Amino acid deletion(s) refers to the deletion of at least one amino acid, such as the deletion of 1 to 10 amino acids, preferably 1 to 5 amino acids, and more preferably 1 to 3 amino acids from an original peptide. Amino acid modification includes, but is not limited to, amidation, carboxylation, sulfation, halogenation, alkylation, glycosylation, phosphorylation, hydroxylation, acylation (e.g., acetylation), and the like. Amino acids to be substituted or added may be naturally-occurring or nonnaturally-occurring amino acids, or amino acid analogs. Naturally-occurring amino acids are preferable.

As used herein, the term "substitution, addition or deletion" for a polypeptide or a polynucleotide refers to the substitution, addition or deletion of an amino acid or its substitute, or a nucleotide or its substitute with respect to the original polypeptide or polynucleotide. This is achieved by techniques well known in the art, including a site-directed mutagenesis technique and the like. A polypeptide or a polynucleotide may have any number (>0) of substitutions, additions, or deletions. The number can be large as long as a variant having such a number of substitutions, additions or deletions maintains an intended function (e.g., cancer marker, nerve disease marker, etc.). For example, such a number may be one or several, and preferably within 20% or 10% of the full length, or no more than 100, no more than 50, no more than 25, or the like.

A macromolecule structure (for example, a polypeptide structure) may be described with reference to configurations in various levels. See, for example, Alberts et al., Molecular Biology of the Cell (third edition, 1994), and, Cantor and Schimmel, Biophysical Chemistry Part I: The Conformation of Biological Macromolecules (1980) for a general discussion on this configuration. The "primary structure" refers to an amino acid sequence of a specific peptide. The "secondary structure" refers to a three-dimensional structure of a polypeptide which is arranged locally within the polypeptide. These structures are generally known as a domain. A domain forms a compact unit of a polypeptide, and typically is a portion of the polypeptide having an amino acid length of 50-350. A typical domain is formed of portions such as β sheet (β strand or the like) and a stretch of α-helix. The "tertiary structure" refers to a perfect three-dimensional structure of a polypeptide monomer. The "quaternary structure" refers to a three-dimensional structure formed by independent noncovalent binding of three-dimensional units. The terms related to anisotropy may be similarly used as the terms known in the field of energy.

A general molecular biological method used in the present invention can be readily carried out by those skilled in the art with reference to Ausubel F. A. et al. (1988), Current Protocols in Molecular Biology, Wiley, New York, N.Y.; Sambrook J. et al., (1987) Molecular Cloning: A Laboratory Manual, 2nd Ed., Cold Spring Harbor Laboratory Press, Cold Spring Harbor, N.Y. and the like.

When a gene is mentioned herein, the term "vector" refers to a substance capable of transferring a polynucleotide sequence of interest to a target cell. An example of such a vector is a vector including a promoter at a position suitable for transcription of polynucleotide of the present invention which is capable of self-replication in a bacterial host cell.

As used herein, the term "expression vector" refers to a nucleic acid sequence comprising a structural gene and a promoter for regulating expression thereof, and in addition, various regulatory elements in a state that allows them to operate within host cells. The regulatory element may include, preferably, terminators and selectable markers. It is well known to those skilled in the art that the type of an expression vector and the type of a regulatory element to be used may vary depending on the host bacterial cell.

The term "recombinant vector" refers to a vector capable of transferring a polynucleotide sequence of interest to a target cell. An example of such a vector is a vector including a promoter at a position suitable for a transcription of polynucleotide of the present invention which is capable of self-replication in a bacterial host cell.

Examples of a "recombinant vector" for a prokaryotic cell include pBTrp2, pBTac1, pBTac2 (available from Roche Molecular Biochemicals), pKK233-2 (Pharmacia), pSE280 (Invitrogen), pGEMEX-1 (Promega), pQE-8 (QIAGEN), pKYP10 (Japanese Laid-Open Publication No. 58-110600), pKYP200 (Agric. Biol. Chem., 48, 669 (1984)), pLSA1 (Agric. Biol. Chem., 53, 277 (1989)), pGEL1 (Proc. Natl. Acad. Sci. USA, 82, 4306 (1985)), pBluescript II SK+ (Stratagene), pBluescript II SK(−) (Stratagene), pTrs30 (FERM BP-5407), pTrs32 (FERM BP-5408), pGHA2 (FERM BP-400), pGKA2 (FERM B-6798), pTerm2 (Japanese Laid-Open Publication No. 3-22979, U.S. Pat. No. 4,686,191, U.S. Pat. No. 4,939,094, U.S. Pat. No. 5,160,735), pEG400 [J. Bacteriol., 172, 2392 (1990)], pGEX (Pharmacia), pET system (Novagen), pSupex, pUB110, pTP5, pC194, pTrxFus (Invitrogen), pMAL-c2 (New England Biolabs), pUC19 [Gene, 33, 103 (1985)], pSTV28 (TaKaRa), pUC118 (TaKaRa), pPA1 (Japanese Laid-Open Publication No. 63-233798), Pinpoint Xa (manufactured by Promega), PAN, PAC (manufactured by Avidity), and the like.

As used herein, the term "promoter" refers to a base sequence which determines the initiation site of transcription of a gene and is a DNA region which directly regulates the frequency of transcription and is the sequence where RNA polymerase binds to initiate transcription. A putative promoter region is usually located upstream of a structural gene, but depending on the structural gene, i.e., a putative promoter region may be located downstream of a structural gene.

As used herein, a "solid phase" refers to a planar support member to which a molecule such as an antibody may be immobilized. For performing detection in the present invention using the principle of surface plasmon resonance, the solid phase may be preferably a material of glass substrate having a metal thin film including gold, silver, or aluminum on one side. For performing detection in the present invention using the principle of quartz-crystal microbalance, a frequency conversion element (for example, quartz oscillator, surface acoustic wave element) is used as a solid phase, to directly bind a receptor. A quartz plate with one side covered with silicone, and the other side provided with a gold electrode is used as a solid phase.

As used herein, a "substrate" refers to a material for constructing a chip or an array of the present invention (preferably, a solid). Therefore, the substrate is within the scope of the concept of the solid phase. A substrate material may be any solid material having a characteristic of binding to biomolecule used in the present invention, with covalent bonding or noncovalent bonding, or a material which may be derivatized to have such a characteristic.

A material for use as a solid phase or a substrate may be any material which can form a solid surface. The material may be, but is not limited to, for example, a glass, a silica, a silicone, a ceramic, a silicon dioxide, a plastic, a metal (including an alloy), a natural or synthetic polymer (for example, polystyrene, cellulose, chitosan, dextran, and nylon) and the like. A substrate may be formed of a plurality of layers of different materials. An inorganic insulating material such as, for example, a glass, a silica glass, an alumina, a sapphire, a forsterite, a silicon carbide, a silicon oxide, a silicon nitride and the like may be used. An organic material such as a polyethylene, an ethylene, a polypropylene, a polyisobutylene, a polyethylene terephthalate, an unsaturated polyester, a resin including fluorine, a polyvinyl chloride, a polyvinylidene chloride, a polyvinyl acetate, a polyvinyl alcohol, a polyvinyl acetal, an acrylic resin, a polyacrylonitrile, a polystyrene, an acetal resin, a polycarbonate, a polyamide, a phenol resin, a urea resin, an epoxy resin, a melamine resin, a styrene-acrylonitrile copolymer, an acrylonitrile butadiene styrene copolymer, a silicone resin, a polyphenylene oxide, a polysulfone, and the like may also be used. In the present invention, a membrane used for blotting, such as a nylon membrane, a nitrocellulose membrane, a PVDF membrane, or the like may also be used. For analyzing a sample having a high-density, it is preferable to use a material having hardness such as a glass. A material which is preferable as a substrate varies depending on various parameters such as measurement devices and the like. Those skilled in the art can appropriately select a suitable material from the various materials mentioned above.

As used herein, a "chip" and a "microchip" can be interchangeably used and refer to a microminiature integrated circuit which has various functions and can be a part of a system. As used herein, a solid phase to which a biotinylated receptor is immobilized is referred to as a receptor chip and/or a receptor microchip.

As used herein, an "array" refers to a pattern of one or more (for example, 1000 or more) arrayed and arranged receptors or a substrate having a pattern (for example, a chip) itself. Among arrays, the one which is patterned on a small substrate (for example, 10×10 mm) is referred to as a microarray. In this specification, the microarray and the array can be interchangeably used. Thus, the array patterned to a substrate larger than the above-mentioned substrate may be referred to as a microarray. For example, an array is constructed from desirable sets of receptors immobilized to a solid phase surface or a membrane. An array preferably includes the same or the different receptors with the number of at least $10^2$, more preferably, at least $10^3$, further preferably, at least $10^4$, and still further preferably, at least $10^5$. Such receptors are arranged on a surface of, preferably 125×80 mm, and more preferably 10×10 mm. Regarding the form, one of a microtiter plate size, such as 96 well microtiter plate, 384 well microtiter plate, or the like, and one of the size about a slide glass are contemplated. Receptors to be immobilized may be 1 type or a plurality of types. The number of types may be any number between 1 to the number of spots. For example, about 10 types, about 100 types, about 500 types, and about 1000 types of receptors may be immobilized.

As described above, on a solid phase surface or a membrane, such as substrate, any number of biomolecules (for example, receptors) may be arranged. Typically, on one substrate, up to $10^6$ biomolecules, in another embodiment, up to $10^7$ biomolecules, up to $10^6$ biomolecules, up to $10^5$ biomolecules, up to $10^4$ biomolecules, up to $10^3$ biomolecules, or up to $10^2$ biomolecules may be arranged. There may be the case where more than $10^8$ biomolecules are arranged. In these cases, it is preferable that a size of the substrate is small. Especially, the size of the spots of the receptors (biomolecules) may be as small as the size of a single biomolecule (the size may be of the order of 1-2 nm). The minimum area of the substrate is determined by the number of biomolecules on the substrate in some cases. In the present invention, a factor which specifically binds to a cell is immobilized in sequence by a covalent bond or a physical interaction in a spot form of, typically, 0.01-10 mm.

On an array, a "spot" of biomolecule may be arranged. As used herein, the "spot" refers to a certain population of biomolecules. As used herein, "spotting" refers to producing a spot of a certain biomolecule on a certain substrate of a solid phase. Spotting may be achieved by any method, for example, by pipetting, or an automatic device. Such methods are well-known in the field of art. As used herein, biomolecules are receptors, fragments of receptors, of derivatives of receptors.

As used herein, the term "address" refers to a unique location on a substrate, which can be distinguished from other unique locations on the substrate. The address is suitable for representing the association of something to the spots, each having an accompanying address. The address may have any form by which a thing at one address can be distinguished from things at other addresses (for example, optically). A form defining the address may be, for example, a circle, an ellipse, a square, a rectangle, or an irregular shape. The "address" can be used for representing an abstract concept, while the "spot" can be used for representing a concrete concept. If there is no need to distinguish one from the other, the "address" and the "spot" may be interchangeably used herein.

The size for defining each address depends on, particularly, the size of the substrate, the number of addresses on a specific substrate, an amount of an analyte and/or an available reagent, the size of micro-particles, and a resolution required for any method in which the array is used. The size may be in the range of, for example, 1-2 nm to several cm. Any size is possible as long as it conforms to an application of the array.

Spatial arrangement and the form defining the addresses are designed so as to adapt to a specific application of the microarray. The addresses may be arranged densely, distributed widely, or divided to subgroups of desirable patterns suitable for a specific types of analyte.

The microarrays are outlined in, Shujunsha, editor, SaiboKogaku [Cell Engineering], Special issue, "DNA Maikuro Arei to Saishin PCR Ho [DNA micro array and Up-to-date PCR Method]"; and M. F. Templin, et al., "Protein microarray technology", Drug Discovery Today, 7(15), 815-822 (2002).

Since an enormous amount of data is obtained from a microarray, data analysis software for managing correspondence between clones and the spots, analyzing data, or the like is important. As such software, software associated to each of detection systems is available (Ermolaeva O et al. (1998) Nat. Genet. 20:19-23). A format of a database may be, for example, a format called GATC (genetic analysis technology consortium) which has been proposed by Affymetrix.

Fine-processing is described in, for example, Campbell, S. A. (1996), The Science and Engineering of Microelectronic Fabrication, Oxford University Press; Zaut, P. V. (1996), Micromicroarray Fabrication: a Practical Guide to Semiconductor Processing, Semiconductor Services; Madou, M. J. (1997), Fundamentals of Microfabrication, CRC1 5 Press; Rai-Choudhury, P. (1997), Handbook of Microlithography, Micromachining, & Microfabrication: Microlithography, or the like. These documents are incorporated herein as reference.

For producing a microarray, various methods such as a micro contact printing method, or an optical lithography method may be used. Preferably, a method using a micropatterned surface of an alkanethiol monomolecular film is used. In this case, first, an alkanethiol monomolecular film having a hydrophobic functional group such as methyl group or fluoromethyl group is formed on a glass substrate with a gold thin film formed on one side by vapor deposition. The monomolecular film is overcoated with a photomask in which a number of light transmissive spots having diameters of about several micrometers to 1 mm are arrayed, and irradiated with an ultraviolet ray. Thus, the alkanethiol of irradiated portions can be degraded and removed in a spot shape. A reactive functional group introduced into a spot is used to immobilize a protein which specially binds to biotin, such as streptavidin, avidin, or the like. Finally, a receptor protein is immobilized through a biotinylated site of a receptor protein, and thus an immobilization of the receptor protein is finished with direc-tivities maintained under moderate conditions without a chemical process. For example, in the case of a spot including a carboxyl group, the carboxyl group is converted to an active ester by using N-hydroxysuccinimide, then avidin, streptavidin or the like is immobilized. Then, a small amount of a solution including biomolecules is dripped to each of the spots. Thus, immobilization is performed. The hydrophobic monomolecular films formed around the spots are effective for suppressing diffusion of a solution. In order to suppress non-specific interactions between background areas around the spots and analytes, an inactive protein such as bovine serum albumin or hydrophilic macromolecule such as polyethylene glycol is used for blocking.

As clearly indicated by the progress in assay techniques using DNA microarrays, a protein chip, or the like, utilizing microarrays is a very effective method of assay since it is possible to perform a high-throughput assay for a number of analytes on one substrate. The present invention applies such a way of using microarrays to a quick measurement of interactions between various types of biomolecules and cells. In this case, integration of micro arrays is important for assaying a very large number of analytes at the same time, or making the amounts of biomolecules and cells required for assay as small as possible. On the other hand, when information related to cells on the micro arrays is obtained, the obtained data has a large error unless the measurement is performed for a subject of a population comprising a certain number of cells. In view of this, it is desirable that the size of spots constructing the microarrays is the size which allows at least several tens to several thousands cells to interact. In the case of a circular spot, for example, its diameter is about several μm to 1 mm.

The microarrays may be produced by various methods such as a micro contact printing method, optical lithography method, or the like. Preferably, a method utilizing a micropatterned surface of an alkanethiol monomolecular film is used.

As used herein, the term "biomolecule" refers to a molecule related to an organism. As used herein, "organism" refers to a biological organism, and includes, but is not limited to, an animal, a plant, a fungi, a virus, or the like. The biomolecule includes a molecule extracted from an organism. However, the biomolecule is not limited thereto, and any molecule which may affect an organism is within the definition of the biomolecule. Such a biomolecule includes, but is not limited to, a protein, a polypeptide, a oligopeptide, a peptide, a polynucleotide, a oligonucleotide, a nucleotide, a nucleic acid (including for example, cDNA, a DNA such as a genome DNA, RNA such as mRNA), a polysaccharide, an oligosaccharide, a lipid, a low molecule (for example, hormone, a ligand, a signal transduction substance, an organic low molecule, a combinatorial library compound, or the like), composite molecules thereof, or the like. Preferable biomolecules as used herein are a receptor and a receptor fragment, and ligands thereof.

As used herein, the "factor specifically binds to biotin" refers to any factor which may specifically bind to a biotin. The bond between a factor capable of specifically binding to biotin and the biotin may be reversible or irreversible. Examples of the factor capable specifically binding to biotin includes, but not limited to, avidin and streptavidin, and variants thereof.

A surface plasmon resonance (SPR) is an interaction between surface plasmon (elastic waves) generated on a metal surface, and evanescent waves (light waves) generated by electromagnetic waves by total internal reflection. When light enters at angle $\theta$, which gives the condition in which wave number and wave motion vector of the plasmon waves and the evanescent waves approximately matches, a resonance occurs. The evanescent waves are used for exciting the surface plasmon, and thus the intensity of reflected light is decreased. In order to obtain a surface plasmon resonance, a method in which a prism comprising a medium of a high refractive index is arranged (Kretschmann arrangement), and laser beam and LED light incident. Herein, due to changes in permittivity of the medium contacting a metal surface on the other side of the prism, the wave number of plasmon waves varies. More specifically, if a substance comes close to the metal surface, an angle of incidence of a light which gives the surface plasmon resonance shifts. By utilizing this fact, it is possible to sense a substance coating the metal surface. Such a measurement method is good at a resolution in a perpendicular direction relative to the surface (order of 0.1 nm), and it is possible to measure the amount of the substance on the surface in order of ng to $pg/cm^2$ in real time. Further, it has a great advantage for examining behavior of biomolecules such as a protein that measurement can be performed in an aqueous medium. A measuring device utilizing this fact has been developed as an interactive measurement device between biomolecules, and applied to assay of interactions between proteins and DNAs.

A quartz-crystal microbalance is a apparatus in which one of a binding pair is chemically bound and immobilized to an electrode of a frequency conversion element, the frequency conversion element is immersed into water, changes in the frequencies of the frequency conversion element due to change in mass generated by a corresponding binding pair specifically binding to the binding pair is measured to detect presence/absence of binding (for example, Japanese Laid-Open Publication No. 6-94591). Such a frequency conversion element may be, for example, a quartz oscillator, a surface acoustic wave element (SAW), or the like.

A receptor chip of the present invention may also be used as a mass spectrometric chip for a mass spectrometer. In general, an assay by mass spectroscopic measurement involves vaporization and ionization of a small amount of sample using a high energy source such as laser, including a laser beam. A substance is vaporized to gas or a vapor phase by a laser beam from a surface of a tip of a mass spectrometric chip. During this process, some of individual molecules gain protons and are ionized. Then, these molecules ionized to a positive charge are accelerated with a short high-voltage electric field and introduced (drifted) to a high-vacuum chamber. Beyond the chamber, the molecules collide against a surface of a highly sensitive detection device. A time of flight is a function of mass of ionized molecules. Thus, a time period from ionization and collision can be used for determining a mass of the molecules. The mass of molecules can be used for determining whether or not a known molecule of a specific mass exists (time of flight mass spectrometric measurement (TOF)). Further, by utilizing the fact that only ions of a specific mass/number of charges (m/Z) included in an ionized sample have a stable vibration state, a mass/number of charges (m/Z) of a sample (or fragment ions of a sample) can be detected, using a mass filter which passes through only ions having a specific mass/number of charges (m/Z) (if necessary, generating fragment ions) by applying a voltage of a direct-current component and an alternate-current component of a high frequency (tandem mass spectrometry).

A method for generating vapor phase ions may be a desorption/ionization method obtained from bombardment of particles to a sample. This method includes a fast atom bombardment method (FAB) (neutral particles bombard against a sample suspended in a volatile matrix), a secondary ion mass spectrometry (SIMS) (keV primary ions bombard a surface to generate secondary ions), a liquid SIMS (LSIMS) (the same as the FAB except for the point that primary species is ion), a plasma desorption mass spectrometry (the same as the SIMS except for the point that MeV primary ion is used), a mass cluster impact method (MC1) (the same as SIMS except for using primary ions of a mass cluster), a laser desorption/ionization method (LDI) (laser beam is used to desorb/ionize species from a surface), a matrix assist laser desorption/ionization method (MALDI) (same as the LDI except for the point that the species is desorbed/ionized from a matrix which can assist events of desorption and ionization), and the like. A typical mass spectrometry may be, a laser desorption/ionization, a method using time of flight mass spectroscopic measurement (TOF).

A measurement method for using a mass spectroscopic chip to which molecules performing affinity binding such as receptors is used in a mass spectrometer disclosed in, for example, Japanese National Phase PCT Laid-Open Publication No. 9-501489, is the method comprising the following steps:

exposing amass spectroscopic chip surface on which receptors are immobilized to a source of the assay subject molecules (for example, a mixture including ligands), and binding the assay subject molecules;

placing a tip of the mass spectroscopic chip to which the assay subject molecules are bound to on one end of a time of flight mass spectroscopic measurement device and generating an accelerating potential in a spectrometer by applying a vacuum and electrical field;

for desorbing ions of the assay subject molecules from the tip, bombarding at least a portion of the assay subject bound to the derivatized tip face of the mass spectroscopic chip in the spectrometer, using one or more laser pulses;

detecting the mass of ions based on time of flight in the mass spectroscopic measurement; and displaying the mass as detected.

According to this method, the mass of ions of the molecule bound to the mass spectroscopic chip (for example, ligands capable of specifically binding to a receptor) can be detected.

In this method, it is possible to measure the mass of the assay subject molecules by laser desorption/ionization, or a time of flight mass spectroscopic measurement method. In this method, in order to facilitate desorption and ionization of the assay subject, an energy absorption material (for example, sinapic acid, a cinnamal amide, a cinnamyl bromide, 2,5-dihydroxybenzoic acid, and α-cyano-4-hydroxy cinnamate) may be used with the assay subject.

Another measurement method for using a mass spectroscopic chip to which molecules performing affinity binding such as receptors is used in a mass spectrometer is disclosed in, for example, Japanese National Phase PCT Laid-Open Publication No. 11-512518. In the disclosed method, affinity binding molecules such as receptors are immobilized to the chip on a surface of a support member having generally a hydrogel, and more particularly, a polysaccharide hydrogel such as carboxymethylated dextran. Then, the analyte (for example, ligands) is brought into contact with the supporting member. The presence/absence of the analyte bound to the affinity binding molecules and the mass thereof are analyzed.

The receptors as used herein may be, but are not limited to, a scavenger receptor including a C-type lectin-like oxidized LDL receptor (LOX-1), a receptor belonging to an insulin receptor family, a receptor belonging to an EGF receptor family, a receptor belonging to a PDGF receptor family, a receptor belonging to a VEGF receptor family, a receptor belonging to an FGF receptor family, a proliferation factor receptor such as NGF receptor family, a TGF-β super family receptor, a Toll-like receptor family, an LDL receptor related protein family, and a G protein coupled receptor family.

In the method as described herein, refolding of a receptor protein expressed as an inclusion body is performed in a solution including a cyclic carbohydrate cycloamylose and a polyoxyethylene detergent, or in a solution including a cyclic carbohydrate cycloamylose and an ionic detergent. As used herein, a lower limit of a degree of polymerization of a cyclic carbohydrate cycloamylose (it may also be referred to as CA) is 17 or more, preferably 25 or more, more preferably 40 or more, and an upper limit of degree of polymerization is 150 or less, preferably 100 or less, more preferably 50 or less.

The polyoxyethylene detergent used herein may be, but is not limited to a polyoxyethylene detergent represented by the general formula $C_nH_{2n+1}(OCH_2CH_2)_xOH$ and typically referred to as a $C_nE_x$, preferably, polyoxyethylene sorbitan ester, polyoxyethylene dodecyl ether, polyoxyethylene heptamethyl hexyl ether, polyoxyethylene isooctyl phenyl ether, polyoxyethylene nonyl phenyl ether, polyoxyethylene fatty acid ester, or sucrose fatty acid ester.

The ionic detergent used herein may be cetyltrimethyl ammonium bromide, dodecyl sodium sulfate, sodium deoxycholate, 3-[(3-cholamidopropyl)dimethylammonio]-1-propane sulfonate, hexadecyltrimethyl ammonium bromide (it may also be referred to as CTAB), myristyl sulfo betaine (it may also be referred to as SB3-14) or the like, and particularly, cationic or ampholytic surface active agents such as CTAB, SB3-14 and the like are preferable. However, the present invention is not limited to these.

Particularly preferable detergents used for refolding to a proper higher-order structure may be polyoxyethylene sorbitan ester, polyoxyethylene dodecyl ether, polyoxyethylene fatty acid ester, or sucrose fatty acid ester, hexadecyltrimethyl ammonium bromide (CTAB), sodium deoxycholate, myristyl sulfo betaine (SB3-14) and the like.

By adding an excess amount of a detergent, a substance which denatures a biotinylated protein and the like is diluted, and aggregation of receptors can be prevented.

The cyclic carbohydrate may be, as described above, cyclic α-1,4-glucan having the degree of polymerization of 17 or more.

One of C-type lectin-like oxidized LDL receptors (LOX-1) which belong to a scavenger receptor family, a human-derived LOX-1 (it may also be referred to as hLOX-1) recognizes and binds to an oxidized LDL, one of modified LDLs which may cause diseases such as arteriosclerosis, and hyperlipemia.

Further, hLOX-1 is also known to recognize abnormal cells such as apoptotic cells or aged erythrocytes, and bacteria which may cause food poisoning or infectious disease such as *Escherichia coli* or *Staphylococcus aureus*. It has been expected that extracellular regions are related to these recognize and bind to ligands, and an essential minimum region for ligand binding is C-type lectin-like domain (it may also be referred to as CTLD).

The present inventors studied the following process: accumulating a large amount of extracellular regions or CTLDs of hLOX-1 as an aggregate of a biotin labeled protein in *E. coli*; unfolding an erroneous structure with a denaturant; and then, refolding into a correct higher-order structure having a ligand recognition ability by using a detergent and cyclic α-1,4-glucan, for example, highly polymerized cycloamylose (it may also be referred to as CA) having a degree of polymerization of 17 or more.

The present inventors also studied the process in which the refolded biotinylated receptors are immobilized on a solid phase through avidin or streptavidin with a directivity maintained, and used as a sensor portion for a detection devices using the principle of, for example, surface plasmon resonance, quartz-crystal microbalance, or the like, for conveniently detecting modified LDLs, abnormal cells, bacteria, or the like.

A chimeric gene is constructed by combining a gene encoding extracellular regions of hLOX-1, or ligand recognition domains (for example, CTLD); and a gene encoding polypeptide to be biotinylated in *E. coli*. The chimeric gene is inserted into an expression vector for *E. coli* and the expression vector is used for transformation of *E. coli*. *E. coli* are cultured in presence of biotin under the condition to induce an expression of biotinylated protein. Biotinylated extracellular regions or biotinylated CTLD are accumulated in a cell body as an inactive aggregate. An erroneous structure is unfolded with a denaturant. Then, a biotinylated protein in a denatured state is treated with a detergent and a cyclic carbohydrate, for example, a cyclic α-1,4-glucan having a degree of polymerization of 17 or more and is converted to have a ligand recognition ability. The biotinylated protein is immobilized through avidin or streptavidin on a solid phase depending on characteristics of the detection device, thereby achieving the problem of the present invention.

In a preferable embodiment of the present invention, the biotinylated protein in the denatured state is a biotinylated scavenger receptor extracellular region produced as an insoluble inclusion body by bacteria, and the insoluble inclusion body is solublized by a denaturant. In a preferable embodiment, the receptor extracellular region is an extracellular region of a human hLOX-1, or CTLD. In these embodiments, a method for using the receptor chip of the present invention as a sensor for detecting modified LDL, abnormal cells such as apoptotic cells, and bacteria is also achieved.

The present invention also teaches a method comprising the steps of: adding an excess amount of detergent to biotinylated receptors in the denatured state to dilute a substance denaturing the receptors and to prevent aggregation of the biotinylated receptors; then adding a cyclic α-1,4-glucan having a degree of polymerization of 17 or more to strip detergent from detergent/protein complex using the inclusion complex forming ability; and refolding the biotinylated receptor to a correct higher-order structure having a ligand recognition ability to use as a sensor.

Therefore, according to the present invention, a method for conveniently detecting modified LDL, abnormal cells such as apoptotic cells, and bacteria, and a detection sensor therefor are provided.

In the method according to the present invention, first, a region related to a ligand recognition site of a receptor is expressed in vivo or in vitro. Herein, the receptor may be a scavenger receptor family, such as LOX-1 or the like. The region related to the ligand recognition site refers to, for example, an extracellular region or a ligand recognition region, such as CTLD.

For expressing the region related to the ligand recognition site of the receptor in vivo or in vitro, an extracellular region of hLOX-1 or a DNA fragment encoding CTLD is prepared by a usual method of the PCR method. At that time, restriction enzyme sites in accordance with an expression vector of a host to be expressed are attached to both terminals of the DNA fragment. For example, in the case of expressing in *E. coli*, restriction enzyme site NruI is attached to 5' terminal, and restriction enzyme site EcoRV is attached to the 3' terminal.

A PCR product is extracted and processed with a corresponding combination of the restriction enzymes. Then, the PCR product is inserted into pBS, a cloning vector which has been processed with similar restriction enzymes, and confirmed by DNA sequencing whether there is no error in a gene sequence.

Then, gene encoding the protein of which the sequence has been confirmed is digested by the corresponding restriction enzymes, and inserted into the restriction enzyme site of the expression vector. The expression vector used herein is, in the case of E. coli, a plasmid vector Pinpoint Xa (manufactured by Promega) encoding polypeptides known to be biotinylated in E. coli. Next, the genes are transformed into E. coli JM109 which is an expression host, and the transformants which have the target gene correctly are selected.

Furthermore, when inserting the genes into the expression vector, the sequence of the polypeptide to be biotinylated is inserted upstream of the gene sequence, so as to enable express as a fusion protein with the biotinylated polypeptide.

Regarding biotinylation, a colony of E. coli JM109 transformed with plasmid of interest is inoculated to 5 ml of a LB culture medium including Ampicillin of a final concentration of 100 μg/ml and 2 μM of biotin, and cultured overnight at 37° C. while stirring. Then, 0.5 ml of the cultured liquid is added to 50 ml of a LB culture medium including Ampicillin of a final concentration of 100 μg/ml and 2 μM of biotin, and cultured for one hour. IPTG is added so as to have the final concentration of 100 μM, inducing the expression of the fusion protein of interest, and cultured for another 4 hours while stirring. Such an operation allows expression of the target protein as the biotinylated protein.

Reconstitution of the region related to the ligand recognition of the receptors accumulated in E. coli is performed as follows. First, an extracellular region or a ligand recognition region of the receptor collected in an insoluble fraction is treated in 6M of guanidine hydrochloride including DTT having a final concentration of 40 mM for one hour to unfold an erroneous structure. Secondly, a 0.05-0.1% detergent solution having a volume 70 times that of unfolded solution (PBS (—) (phosphate buffer saline (PBS), from which CaCl$_2$ and MgSO$_4$ are removed) including DL-cystine having a final concentration of 2 mM) is added, and reacted at room temperature for one hour.

During this process, a denaturant is diluted, while aggregation of the receptors due to dilution of the denaturant is prevented by the added detergent forming a receptor/detergent complex. Finally, 3% CA preservation solution is added so as to obtain a final concentration of 0.6%, the mixture is reacted at room temperature for one hour. CA peels off the detergent from the receptor/detergent complex. With this process, the receptors are refolded into correct a tertiary structure, and thus, reconstituted receptors can be obtained.

The denaturant may be guanidine hydrochloride, urea or the like. In order to completely unfold an erroneous structure, guanidine hydrochloride of a final concentration of 6M is generally used. In order to cut any S—S bond which is erroneously formed, DTT of a final concentration of 40 mM is added to the denaturant solution. A concentration of protein to be processed, is about 10 mg/ml. An inclusion body is suspended in PBS (—) (phosphate buffer saline (PBS), from which CaCl$_2$ and MgSO$_4$ are removed). Then, guanidine hydrochloride of a final concentration of 6M including DTT of a final concentration of 40 mM is added, and the mixture is reacted at room temperature for one hour.

Next, the expressed protein is utilized to detect modified LDL such as oxidized LDL, abnormal cells such as apoptotic cells or aged erythrocytes, and bacteria (for example, pathogenic bacteria, which may cause food poisoning or infectious disease after invading into organism).

For detection, the detection sensor is prepared. In a preferable embodiment of a method for preparing a sensor detecting modified LDL, abnormal cells such as apoptotic cells, and bacteria according to the present invention, a region related to a ligand recognition site of the receptors may be expressed in vivo or in vitro as a biotinylated protein.

The expressed biotinylated protein, for example, the extracellular region or CTLD of hLOX-1 are accumulated in E. coli as an inclusion body. Then, as described above, the denaturant such as guanidine hydrochloride is used to unfold the erroneous higher-order structure. Subsequently, an excess amount of a detergent is added to the biotinylated extracellular region or CTLD in the denatured state. A substance which denatures a biotinylated protein is diluted, and aggregation of receptor molecules can be prevented.

Next, a cyclic carbohydrate, for example, a cyclic α-1,4-glucan having a degree of polymerization of 17 or more is added to strip detergent from detergent/protein complex by using the inclusion complex forming ability. The protein is refolded into correct higher-order structure, and converted to have a ligand recognition ability. Thereafter, the protein is immobilized on a solid phase such as a chip, a cuvette or the like through avidin or streptavidin with a directivity maintained, the obtained chip is used as a sensor (i.e., a receptor chip).

For constructing a sensor site of interest in the receptor chip, the present inventors have expected that the extracellular region or CTLD of the hLOX-1 can bind modified LDL, abnormal cells, and bacteria by itself and established the conditions for conveniently and inexpensively producing the extracellular region and CTLD of the hLOX-1.

The present inventors considered that, in order to produce the regions which can be widely used as the sensor site, it is possible to utilize immobilization through avidin or streptavidin in the entire system for analyzing interaction of proteins or the like, thus the inventors prepared a region of protein to be immobilized as the biotinylated protein.

Thus, as a system which can express the extracellular region or CTLD of the hLOX-1 as a biotinylated protein, the inventor tried to express the extracellular region or CTLD as a fusion protein with polypeptide biotinylated in E. coli in the presence of biotin.

As a result, any of the biotinylated proteins can be expressed in an excess amount, but it is shown that the biotinylated proteins accumulate in E. coli body as an irregular aggregate (inclusion body), and thus they have to be refolded to a state having a ligand recognition ability.

In the next step, the biotinylated protein in which an inclusion body is formed is refolded. The result is better than that of an artificial chaperone method.

Reconstituted biotinylated extracellular region, and biotinylated CTLD are suggested to have recovered the ligand recognition abilities and can function as a sensor.

Next, the reconstituted biotinylated extracellular region, and the biotinylated CTLD are considered as to whether they can actually function as the sensor sites. They are immobilized to a system through avidin or streptavidin. The system is capable of monitoring binding to ligand as a numerical value. Binding to various types of ligands were considered.

As a result, in the case of oxidized LDL or acetylated LDL, it is shown that they can be detected even at a low concentration of 50 ng/ml ($10e^{-11}$ M). Further, it is shown that apoptotic cells, and bacteria such as E. coli, Staphylococcus aureus can be detected.

As a detection device used for the above detection method, it is possible to use a device which is generally used for analyzing interaction between molecules, such as, a surface plasmon resonance, quartz-crystal microbalance, mass spectrometer, or the like.

For detecting modified LDL, abnormal cells such as apoptotic cells and bacteria, first, a biotinylated region or biotinylated CTLD which has been successfully refolded is immobilized to a sensor site of a device which is capable to perform a quantitative detection. In the case of a device utilizing the principle of surface plasmon resonance, the biotinylated region or the biotinylated CTLD is immobilized on a chip or a cuvette, which conforms to a shape of an insertion site of the device through streptavidin or avidin so that the ligand recognition regions are directed outward. In the case where quartz-crystal microbalance is used for detection, the biotinylated region or the biotinylated CTLD is immobilized on a quartz oscillator, which can be inserted into the device, through streptavidin or avidin so that the ligand recognition regions are directed outward.

These sensor sites are respectively inserted into detection devices. The modified LDL (oxidized LDL, acetylated LDL), apoptotic cells (apoptosis is induced by processing HL60 with a cycloheximide), or bacteria (*E. coli, S. aureus*, and the like) are added or flow in a flow path, and thus, binding is measured. In the case of a device using the principle of a surface plasmon resonance, binding is detected as a change in a refractive index at a sensor surface due to ligand binding (resonance unit; RU). In the case of the device using the principle of quartz-crystal microbalance, since the weight load increases, binding is detected as a decrease in a frequency (Hz).

Example 1

Hereinafter, the present invention will be described in detail with reference to the examples, but it should be noted that the present invention is not limited to these examples.

Expression of a biotinylated extracellular region, and a biotinylated CTLD of hLOX-1

In the present example, the method for expressing an extracellular region, and a CTLD of hLOX-1 as a biotinylated protein is considered.

(1) Construction of an Expression System for a Fusion Protein of a Biotinylated Polypeptide and an Extracellular Region or CTLD of hLOX-1

A DNA fragment encoding an extracellular region or CTLD of hLOX-1 is prepared by a usual method of the PCR method. Restriction enzyme site NruI is attached to 5' terminal, and restriction enzyme site EcoRV is attached at the 3' terminal. A PCR product is extracted and processed with both of the restriction enzymes. Then, the PCR product is inserted into pBS, a cloning vector, and confirmed by a DNA sequencing whether there is no error in a gene sequence. A base sequence and amino acid sequence of the extracellular region of hLOX-1 is represented by SEQ ID NOs:1 and 2 in the sequence list, and a base sequence and amino acid sequence of the CTLD of the hLOX-1 is represented by SEQ ID NOs:3 and 4 in the sequence list. Then, the gene encoding the protein of which the sequence has been confirmed is digested by the restriction enzymes, and inserted into the restriction enzyme site of plasmid vector Pinpoint Xa (manufactured by Promega) encoding polypeptides known to be biotinylated in *E. coli*. Next, the genes are transformed into *E. coli* JM109 which is an expression host, and the transformants which take up the gene of interest correctly are selected.

(2) An Induction Method for a Biotinylated Protein

A colony of *E. coli* JM109 transformed with the plasmid of interest is inoculated into 5 ml of a LB culture medium including Ampicillin of a final concentration of 100 µg/ml and 2 µM of biotin, and cultured overnight at 37° C. while stirring. Then, the cultured liquid is inoculated into 50 ml of a LB culture medium including Ampicillin of a final concentration of 100 µg/ml and 2 µM of biotin in a ratio of 1:100 (volume ratio) and cultured for one hour. Then, IPTG is added so as to obtain a final concentration of 100 µM, inducing the expression of the fusion protein of interest, and cultured for another 4 hours while stirring.

(3) Detection and Confirmation of Expression of the Biotinylated Extracellular Region and the Biotinylated CTLD After induction, 100 µl of the cultured medium is put into a 1.5 ml centrifuge tube and subjected to centrifugation at a 15,000 rpm and the cells are collected. The collected cells are disrupted with ultrasonic waves. A supernatant (soluble fragment) and a precipitate (an insoluble fragment) obtained by subjecting cell bodies to centrifugation at 20,000 g for 30 minutes, are respectively suspended in an SDS sample buffer, and processed at 95° C. for four minutes. Then, a protein is separated by 12% SDS-PAGE, and electrically transferred to a nitrocellulose membrane.

The transferred nitrocellulose membrane is dyed with *ponceau S*, and a location of a protein band is confirmed. Then, transferred nitrocellulose membrane is stirred gently in TBS-Tween (20 mM of Tris, 150 mM of NaCl, pH 7.6, 0.10 Tween 20) at room temperature for 60 minutes. Next, the transferred nitrocellulose membrane is reacted in a streptavidin labeled alkali phosphatase at room temperature for 30 minutes. Subsequently, after reaction, a nitrocellulose membrane is washed with TBS-Tween. Then, a substrate of alkali phosphatase, a NBT/BCIP solution, is added thereto, and reacted at room temperature until a band of the biotinylated protein is detected. As a result, in the insoluble fragment, a significant band of a biotinylated protein is detected at a position corresponding to molecular weights of the biotinylated extracellular region, and biotinylated CTLD.

Example 2

Reconstruction of the Biotinylated Extracellular Region and the Biotinylated CTLD to Soluble Proteins It is shown that the expressed biotinylated extracellular region and the biotinylated CTLD are not present in the soluble fragment in the *E. coli*, and most of them are accumulated as an inclusion body. Therefore, the biotinylated extracellular region, and the biotinylated CTLD is refolded from inclusion body by an artificial chaperone method.

The inclusion body is processed at room temperature for one hour with 6 M of guanidine hydrochloride solution including DTT of a final concentration of 40 mM, and erroneous structure is completely unfolded. Then, a detergent solution having a volume 70 times that of unfolded solution (PBS solution(—) including 0.1% CTAB or SB3-14, DL-cystine having a final concentration of 2 mM) is added, and reacted at room temperature for one hour. Then, 24 ml of reaction solution is removed, and 6 ml of 3% CA solution is added and reacted for another one hour at room temperature.

Figure 2B:
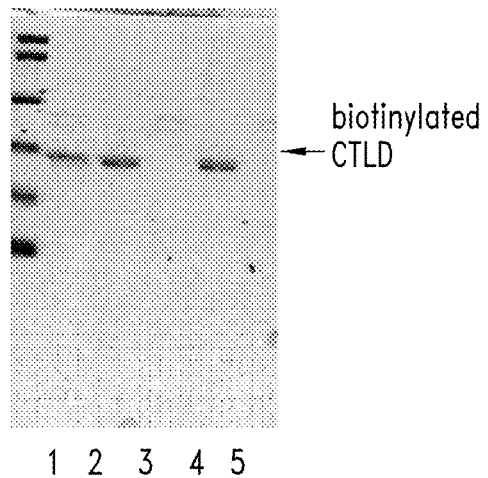
Figure 3A:
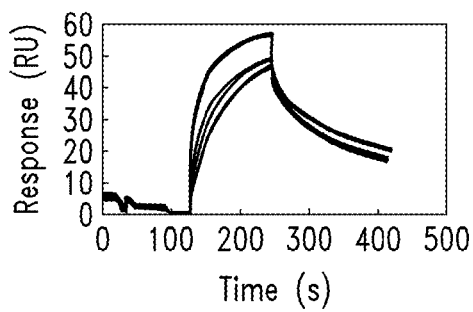
FIG. 3 shows a graph indicating the result of detection of modified LDL by surface plasmon resonance in Example 3. A: Result of detection of acetylated LDL by the extracellular region. B: Result of detection of oxidized LDL by the extracellular region. C: Result of detection of acetylated LDL by the CTLD. D: Result of detection of oxidized LDL by the CTLD.
Figure 3B:
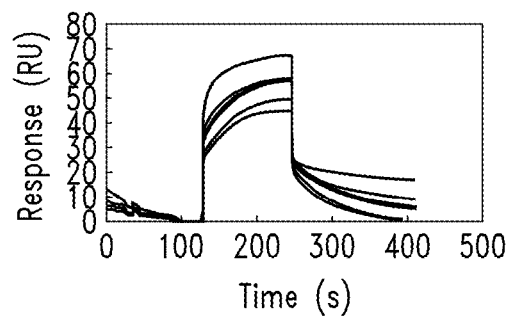
Figure 3C:
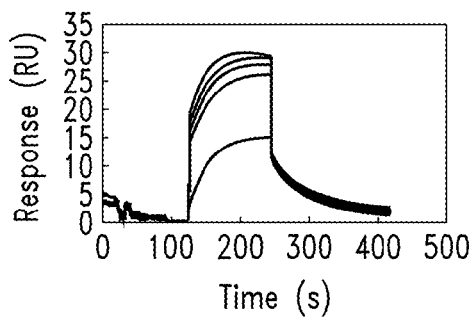
Figure 3D:
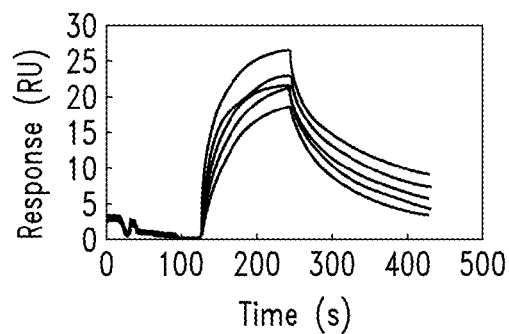

The solution is subjected to centrifugation at 20,000 g for 10 minutes, and the obtained supernatant (soluble fraction) is used as a refolding solution. The presence/absence of the biotinylated extracellular region, and the CTLD is confirmed. It is confirmed that 80% or more is collected in the soluble fraction. An effective refolding is indicated (FIG. 2).

The refolded biotinylated extracellular region, and the biotinylated CTLD are immobilized on streptavidin beads. Binding of the fluorescent labeled acetylated LDL (one of the ligands), DiI AcLDL, are confirmed. Fluorescence is observed on beads on which the refolded biotinylated extracellular region, and the biotinylated CTLD region are immobilized, indicating both of them have recovered ligand binding abilities.

Example 3

The successfully refolded biotinylated extracellular region or biotinylated CTLD was immobilized onto a sensor site of a device capable of detecting the binding by surface plasmon resonance in order to construct a sensor for detecting a modified LDL or the like. Thereafter, the actual binding of a ligand was investigated. As the surface plasmon resonance device, BIACORE (manufactured by BIACORE) and IAsys (manufactured by Hitachi High-Technologies Corporation) were employed.

(1) The reconstituted biotinylated extracellular region was immobilized on a streptavidin sensor chip of BIACORE so that a portion of the region involved in ligand recognition was oriented toward the outside. After the chip was inserted into the BIACORE main body, the binding of modified LDLs (oxidized LDL and acetylated LDL) with the protein was measured. In the case of the device utilizing the principle of surface plasmon resonance, the binding of the ligand was detected as a result of an increase in resonance unit (RU). The binding of modified LDL having various concentrations was investigated. As a result, a modified LDL having a concentration of as low as 50 ng/ml ($10^{-11}$ M) could be well detected (FIG. 3).

(2) The reconstituted biotinylated receptor was immobilized via streptavidin on a biotin cuvette of IAsys so that a portion of the region involved in ligand recognition was oriented toward the outside. After the cuvette was inserted into the IAsys main body, the binding of modified LDLs (oxidized LDL and acetylated LDL) with the protein was measured. As a result, a modified LDL having a concentration of as low as 50 ng/ml ($10^{-11}$ M) could be well detected as in BIACORE.

(3) The reconstituted biotinylated receptor was immobilized via streptavidin on a biotin cuvette of IAsys so that a portion of the region involved in ligand recognition was oriented toward the outside. After the cuvette was inserted into the IAsys main body, the binding of the protein with bacteria (*E. coli* and *Staphylococcus aureus*) was measured. As a result, it was confirmed that the protein bound to either of *E. coli* (gram-negative bacterium) and *Staphylococcus aureus* (gram-positive bacterium).

(4) The reconstituted biotinylated receptor was immobilized via streptavidin on a biotin cuvette of IAsys so that a portion of the region involved in ligand recognition was oriented toward the outside. After the cuvette was inserted into the IAsys main body, the binding of the protein with apoptosis-induced HL60 was measured. As a result, it was confirmed that the protein was bound to apoptosis-induced HL60, but not healthy HL60 in which apoptosis is not induced.

Example 4

The successfully refolded biotinylated extracellular region or biotinylated CTLD was immobilized onto a sensor site of a device capable of detecting the binding by quartz-crystal microbalance in order to construct a sensor for detecting a modified LDL or the like. Thereafter, the actual binding of an ligand was investigated. As the quartz-crystal microbalance device, AffinixQ (manufactured by Intium) was employed.

Figure 4A:
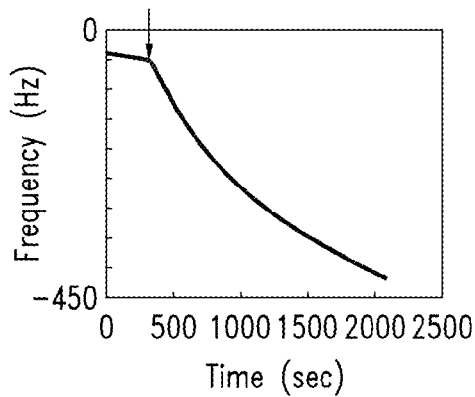
FIG. 4 shows a graph indicating the result of detection of modified LDL by quartz-crystal microbalance in Example 4. A: Result of detection of oxidized LDL by the extracellular region. B: Result of detection of oxidized LDL by the CTLD.
Figure 4B:
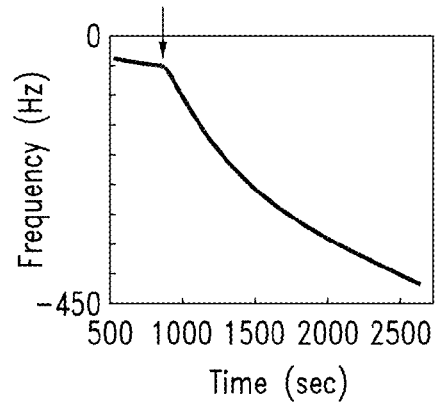

(1) The reconstituted biotinylated receptor was immobilized via streptavidin on a quartz oscillator so that a portion of the region involved in ligand recognition was oriented toward the outside. After the quartz oscillator was inserted into the device, the binding of modified LDLs (oxidized LDL and acetylated LDL) with the protein was measured. As a result, a modified LDL having a concentration of as low as 50 ng/ml ($10^{-11}$ M) could be well detected (FIG. 4).

Figure 5A:
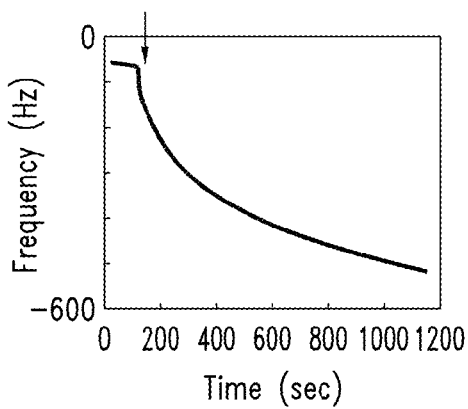
FIG. 5 shows a graph indicating the result of detection of bacteria by quartz-crystal microbalance in Example 4. A: Result of detection of E. coli by the extracellular region. B: Result of detection of S. aureus by the extracellular region.
Figure 5B:
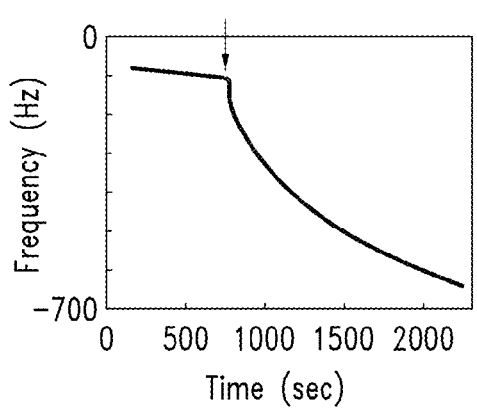
Figure 6A:
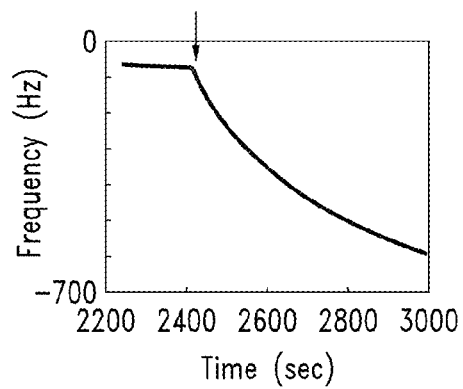
FIG. 6 shows a graph indicating the result of detection of bacteria by quartz-crystal microbalance in Example 4. A: Result of detection of E. coli by the CTLD. B: Result of detection of S. aureus by the CTLD.
Figure 6B:
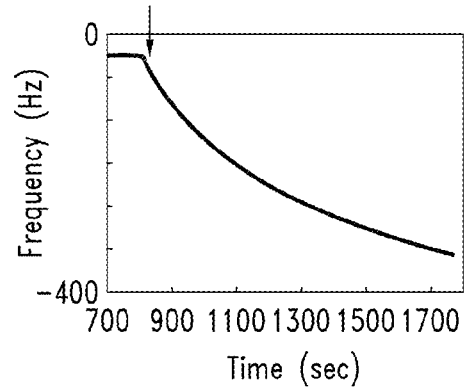

(2) The reconstituted biotinylated receptor was immobilized via streptavidin on a quartz oscillator so that a portion of the region involved in ligand recognition was oriented toward the outside. In the case of a device utilizing the principle of quartz oscillation, when a ligand binds to the protein, the weight of the protein is increased so that the binding is detected as a reduction in frequency (Hz). After the quartz oscillator was inserted into the device, the binding of bacteria (*E. coli* and *Staphylococcus aureus*) with the protein was measured. As a result, it was confirmed that the protein was bound to either of *E. coli* (gram-negative bacterium) and *Staphylococcus aureus* (gram-positive bacterium) (FIGS. 5 and 6). Note that arrows in FIGS. 5 and 6 indicate the time of addition of the bacteria.

Figure 7A:
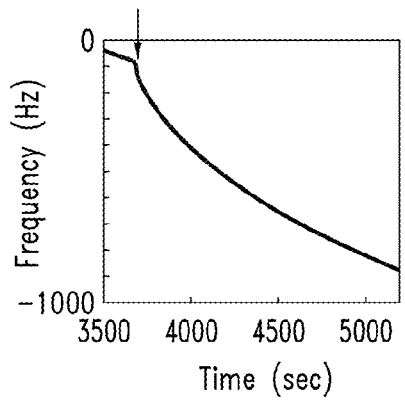
FIG. 7 shows a graph indicating the result of detection of apoptotic cells by quartz-crystal microbalance in Example 4. A: Result of detection of apoptotic cells by the extracellular region. B: Result of detection of apoptotic cells by the CTLD.
Figure 7B:
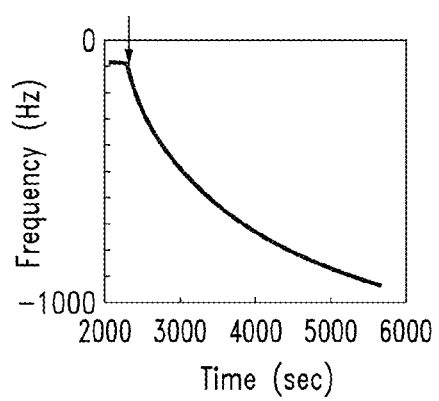

(3) The reconstituted biotinylated receptor was immobilized via streptavidin on a crystal oscillator so that a portion of the region involved in ligand recognition was oriented toward the outside. After the quartz oscillator was inserted into the device, the binding of the protein with apoptosis-induced HL60 was measured. As a result, it was confirmed that the protein was bound to apoptosis-induced HL60, but not healthy HL60 in which apoptosis is not induced (FIG. 7). In FIG. 7, an arrow indicates the time of addition of an apoptotic cell.

In the present invention, a large amount of biotinylated receptor proteins capable of being easily immobilized on a solid phase were prepared and were immobilized on a solid phase to produce a receptor chip. A detection kit and detection method using the chip were provided by the present invention.

The present invention provides a method for efficiently detecting modified LDL accumulated in an organism, abnormal cells, such as apoptotic cells or aged erythrocytes, bacteria invading an organism, and the like. The method can be achieved by employing recombinant proteins obtained by expressing a region of a scavenger receptor relating to a ligand recognition site in vivo or in vitro.

The present invention can supply a large amount of inexpensive sensor site (detection kit) for detecting modified LDL, abnormal cells, and bacteria.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for producing a receptor chip, comprising the steps of:
   (a) recombinantly expressing a biotinylated receptor protein as an inclusion body within a bacterial host, wherein the receptor is a scavenger receptor LOX-1;
   (b) refolding the inclusion body in a solution containing a cyclic carbohydrate cycloamylose and myristyl sulfo betaine to prepare a soluble biotinylated receptor protein; and
   (c) immobilizing the refolded soluble biotinylated protein to a solid phase via a factor capable of specifically binding to biotin.

2. The method according to claim 1, wherein the degree of polymerization of the carbohydrate cycloamylose is 17 to 50 or 40 to 150.

3. The method according to claim 2, wherein the degree of polymerization of the cyclic carbohydrate cycloamylose is 40 to 150.

4. The method according to claim 1, wherein the solid phase is adapted for detection using a surface plasmon resonance device, a quartz-crystal microbalance, or a mass spectrometer.

* * * * *

SEQUENCE LISTING

<160> NUMBER OF SEQ ID NOS: 10

<210> SEQ ID NO 1
<211> LENGTH: 639
<212> TYPE: DNA
<213> ORGANISM: Homo sapiens
<220> FEATURE:
<221> NAME/KEY: source
<222> LOCATION: (1)...(639)
<223> OTHER INFORMATION: aortic endothelial cell
<220> FEATURE:
<221> NAME/KEY: CDS
<222> LOCATION: (1)...(639)

<400> SEQUENCE: 1

```
tcc cag gtg tct gac ctc cta aca caa gag caa gca aac cta act cac      48
Ser Gln Val Ser Asp Leu Leu Thr Gln Glu Gln Ala Asn Leu Thr His
 1               5                  10                  15 cag aaa aag aaa ctg gag gga cag atc tca gcc cgg caa caa gca gaa      96
Gln Lys Lys Lys Leu Glu Gly Gln Ile Ser Ala Arg Gln Gln Ala Glu
             20                  25                  30 gaa gct tca cag gag tca gaa aac gaa ctc aag gaa atg ata gaa acc     144
Glu Ala Ser Gln Glu Ser Glu Asn Glu Leu Lys Glu Met Ile Glu Thr
         35                  40                  45 ctt gct cgg aag ctg aat gag aaa tcc aaa gag caa atg gaa ctt cac     192
Leu Ala Arg Lys Leu Asn Glu Lys Ser Lys Glu Gln Met Glu Leu His
     50                  55                  60 cac cag aat ctg aat ctc caa gaa aca ctg aag aga gta gca aat tgt     240
His Gln Asn Leu Asn Leu Gln Glu Thr Leu Lys Arg Val Ala Asn Cys
 65                  70                  75                  80 tca gct cct tgt ccg caa gac tgg atc tgg cat gga gaa aac tgt tac     288
Ser Ala Pro Cys Pro Gln Asp Trp Ile Trp His Gly Glu Asn Cys Tyr
                 85                  90                  95 cta ttt tcc tcg ggc tca ttt aac tgg gaa aag agc caa gag aag tgc     336
Leu Phe Ser Ser Gly Ser Phe Asn Trp Glu Lys Ser Gln Glu Lys Cys
            100                 105                 110 ttg tct ttg gat gcc aag ttg ctg aaa att aat agc aca gct gat ctg     384
Leu Ser Leu Asp Ala Lys Leu Leu Lys Ile Asn Ser Thr Ala Asp Leu
        115                 120                 125 gac ttc atc cag caa gca att tcc tat tcc agt ttt cca ttc tgg atg     432
Asp Phe Ile Gln Gln Ala Ile Ser Tyr Ser Ser Phe Pro Phe Trp Met
    130                 135                 140 ggg ctg tct cgg agg aac ccc agc tac cca tgg ctc tgg gag gac ggt     480
Gly Leu Ser Arg Arg Asn Pro Ser Tyr Pro Trp Leu Trp Glu Asp Gly
145                 150                 155                 160 tct cct ttg atg ccc cac tta ttt aga gtc cga ggc gct gtc tcc cag     528
Ser Pro Leu Met Pro His Leu Phe Arg Val Arg Gly Ala Val Ser Gln
                165                 170                 175 aca tac cct tca ggt acc tgt gca tat ata caa cga gga gct gtt tat     576
Thr Tyr Pro Ser Gly Thr Cys Ala Tyr Ile Gln Arg Gly Ala Val Tyr
            180                 185                 190 gcg gaa aac tgc att tta gct gcc ttc agt ata tgt cag aag aag gca     624
Ala Glu Asn Cys Ile Leu Ala Ala Phe Ser Ile Cys Gln Lys Lys Ala
        195                 200                 205 aac cta aga gca cag                                                 639
Asn Leu Arg Ala Gln
    210
```

<210> SEQ ID NO 2
<211> LENGTH: 213
<212> TYPE: PRT
<213> ORGANISM: Homo sapiens -continued

```
<400> SEQUENCE: 2

Ser Gln Val Ser Asp Leu Leu Thr Gln Glu Gln Ala Asn Leu Thr His
1               5                   10                  15

Gln Lys Lys Lys Leu Glu Gly Gln Ile Ser Ala Arg Gln Gln Ala Glu
            20                  25                  30

Glu Ala Ser Gln Glu Ser Glu Asn Glu Leu Lys Glu Met Ile Glu Thr
        35                  40                  45

Leu Ala Arg Lys Leu Asn Glu Lys Ser Lys Gln Met Glu Leu His
    50                  55                  60

His Gln Asn Leu Asn Leu Gln Glu Thr Leu Lys Arg Val Ala Asn Cys
65                  70                  75                  80

Ser Ala Pro Cys Pro Gln Asp Trp Ile Trp His Gly Glu Asn Cys Tyr
                85                  90                  95

Leu Phe Ser Ser Gly Ser Phe Asn Trp Glu Lys Ser Gln Glu Lys Cys
            100                 105                 110

Leu Ser Leu Asp Ala Lys Leu Leu Lys Ile Asn Ser Thr Ala Asp Leu
        115                 120                 125

Asp Phe Ile Gln Gln Ala Ile Ser Tyr Ser Ser Phe Pro Phe Trp Met
    130                 135                 140

Gly Leu Ser Arg Arg Asn Pro Ser Tyr Pro Trp Leu Trp Glu Asp Gly
145                 150                 155                 160

Ser Pro Leu Met Pro His Leu Phe Arg Val Arg Gly Ala Val Ser Gln
                165                 170                 175

Thr Tyr Pro Ser Gly Thr Cys Ala Tyr Ile Gln Arg Gly Ala Val Tyr
            180                 185                 190

Ala Glu Asn Cys Ile Leu Ala Ala Phe Ser Ile Cys Gln Lys Lys Ala
        195                 200                 205

Asn Leu Arg Ala Gln
    210

<210> SEQ ID NO 3
<211> LENGTH: 393
<212> TYPE: DNA
<213> ORGANISM: Homo sapiens
<220> FEATURE:
<221> NAME/KEY: source
<222> LOCATION: (1)...(393)
<223> OTHER INFORMATION: aortic endothelial cell
<220> FEATURE:
<221> NAME/KEY: CDS
<222> LOCATION: (1)...(393)

<400> SEQUENCE: 3 cct tgt ccg caa gac tgg atc tgg cat gga gaa aac tgt tac cta ttt     48
Pro Cys Pro Gln Asp Trp Ile Trp His Gly Glu Asn Cys Tyr Leu Phe
1               5                   10                  15 tcc tcg ggc tca ttt aac tgg gaa aag agc caa gag aag tgc ttg tct     96
Ser Ser Gly Ser Phe Asn Trp Glu Lys Ser Gln Glu Lys Cys Leu Ser
            20                  25                  30 ttg gat gcc aag ttg ctg aaa att aat agc aca gct gat ctg gac ttc    144
Leu Asp Ala Lys Leu Leu Lys Ile Asn Ser Thr Ala Asp Leu Asp Phe
        35                  40                  45 atc cag caa gca att tcc tat tcc agt ttt cca ttc tgg atg ggg ctg    192
Ile Gln Gln Ala Ile Ser Tyr Ser Ser Phe Pro Phe Trp Met Gly Leu
    50                  55                  60 tct cgg agg aac ccc agc tac cca tgg ctc tgg gag gac ggt tct cct    240
Ser Arg Arg Asn Pro Ser Tyr Pro Trp Leu Trp Glu Asp Gly Ser Pro
65                  70                  75                  80
```

```
ttg atg ccc cac tta ttt aga gtc cga ggc gct gtc tcc cag aca tac       288
Leu Met Pro His Leu Phe Arg Val Arg Gly Ala Val Ser Gln Thr Tyr
                85                  90                  95 cct tca ggt acc tgt gca tat ata caa cga gga gct gtt tat gcg gaa       336
Pro Ser Gly Thr Cys Ala Tyr Ile Gln Arg Gly Ala Val Tyr Ala Glu
            100                 105                 110 aac tgc att tta gct gcc ttc agt ata tgt cag aag aag gca aac cta       384
Asn Cys Ile Leu Ala Ala Phe Ser Ile Cys Gln Lys Lys Ala Asn Leu
        115                 120                 125 aga gca cag                                                            393
Arg Ala Gln
    130

<210> SEQ ID NO 4
<211> LENGTH: 131
<212> TYPE: PRT
<213> ORGANISM: Homo sapiens

<400> SEQUENCE: 4

Pro Cys Pro Gln Asp Trp Ile Trp His Gly Glu Asn Cys Tyr Leu Phe
1               5                   10                  15

Ser Ser Gly Ser Phe Asn Trp Glu Lys Ser Gln Glu Lys Cys Leu Ser
            20                  25                  30

Leu Asp Ala Lys Leu Leu Lys Ile Asn Ser Thr Ala Asp Leu Asp Phe
        35                  40                  45

Ile Gln Gln Ala Ile Ser Tyr Ser Ser Phe Pro Phe Trp Met Gly Leu
    50                  55                  60

Ser Arg Arg Asn Pro Ser Tyr Pro Trp Leu Trp Glu Asp Gly Ser Pro
65                  70                  75                  80

Leu Met Pro His Leu Phe Arg Val Arg Gly Ala Val Ser Gln Thr Tyr
                85                  90                  95

Pro Ser Gly Thr Cys Ala Tyr Ile Gln Arg Gly Ala Val Tyr Ala Glu
            100                 105                 110

Asn Cys Ile Leu Ala Ala Phe Ser Ile Cys Gln Lys Lys Ala Asn Leu
        115                 120                 125

Arg Ala Gln
    130

<210> SEQ ID NO 5
<211> LENGTH: 126
<212> TYPE: PRT
<213> ORGANISM: Artificial Sequence
<220> FEATURE:
<223> OTHER INFORMATION: Biotinylation motif for biotinylating a protein
      in E. Coli

<400> SEQUENCE: 5

Met Lys Leu Lys Val Thr Val Asn Gly Thr Ala Tyr Asp Val Asp Val
1               5                   10                  15

Asp Val Asp Lys Ser His Glu Asn Pro Met Gly Thr Ile Leu Phe Gly
            20                  25                  30

Gly Gly Thr Gly Gly Ala Pro Ala Pro Ala Ala Gly Gly Ala Gly Ala
        35                  40                  45

Gly Lys Ala Gly Glu Gly Glu Ile Pro Ala Pro Leu Ala Gly Thr Val
    50                  55                  60

Ser Lys Ile Leu Val Lys Glu Gly Asp Thr Val Lys Ala Gly Gln Thr
65                  70                  75                  80
```

```
Val Leu Val Leu Glu Ala Met Lys Met Glu Thr Glu Ile Asn Ala Pro
                85                  90                  95

Thr Asp Gly Lys Val Glu Lys Val Leu Val Lys Glu Arg Asp Ala Val
            100                 105                 110

Gln Gly Gly Gln Gly Leu Ile Lys Ile Gly Asp Leu Glu Leu
        115                 120                 125

<210> SEQ ID NO 6
<211> LENGTH: 15
<212> TYPE: PRT
<213> ORGANISM: Artificial Sequence
<220> FEATURE:
<223> OTHER INFORMATION: Biotinylation motif for biotinylating a protein
      in E. Coli

<400> SEQUENCE: 6

Gly Leu Asn Asp Ile Phe Glu Ala Gln Lys Ile Glu Trp His Glu
1               5                   10                  15

<210> SEQ ID NO 7
<211> LENGTH: 5
<212> TYPE: PRT
<213> ORGANISM: Artificial Sequence
<220> FEATURE:
<223> OTHER INFORMATION: Biotinylation motif for biotinylating a protein
      in E. Coli

<400> SEQUENCE: 7

Lys Ile Gly Asp Pro
1               5

<210> SEQ ID NO 8
<211> LENGTH: 5
<212> TYPE: PRT
<213> ORGANISM: Artificial Sequence
<220> FEATURE:
<223> OTHER INFORMATION: Biotinylation motif for biotinylating a protein
      in E. Coli

<400> SEQUENCE: 8

Lys Leu Trp Ser Ile
1               5

<210> SEQ ID NO 9
<211> LENGTH: 4
<212> TYPE: PRT
<213> ORGANISM: Artificial Sequence
<220> FEATURE:
<223> OTHER INFORMATION: Recognition sequence used to purify an
      exogenous protein

<400> SEQUENCE: 9

Ile Glu Gly Arg
1

<210> SEQ ID NO 10
<211> LENGTH: 5
<212> TYPE: PRT
<213> ORGANISM: Artificial Sequence
<220> FEATURE:
<223> OTHER INFORMATION: Recognition sequence used to purify an
      exogenous protein

<400> SEQUENCE: 10

Asp Asp Asp Asp Lys
1               5
```